US007425415B2

(12) United States Patent
Pfeifer et al.

(10) Patent No.: US 7,425,415 B2
(45) Date of Patent: Sep. 16, 2008

(54) METHOD FOR DETECTING METHYLATED CPG ISLANDS

(75) Inventors: Gerd P. Pfeifer, Bradbury, CA (US); Tibor Rauch, Arcadia, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 11/398,765

(22) Filed: Apr. 6, 2006

(65) Prior Publication Data

US 2006/0240460 A1    Oct. 26, 2006

Related U.S. Application Data

(60) Provisional application No. 60/668,572, filed on Apr. 6, 2005.

(51) Int. Cl.
*C12Q 1/68* (2006.01)
*C12P 19/34* (2006.01)

(52) U.S. Cl. .......................................... 435/6; 435/91.2

(58) Field of Classification Search ....................... None
See application file for complete search history.

(56) References Cited

U.S. PATENT DOCUMENTS

2006/0204988 A1*    9/2006    Fassbender et al. ............. 435/6

OTHER PUBLICATIONS

Matarazzo et al., "In vivo analysis of DNA methylation patterns recognized by specific proteins: coupling ChIP and bisulfite analysis," Biotechniques, Oct. 2004, vol. 37, No. 4.*
Jiang et al., "MBD3L1 Is a Transcriptional Repressor That Interacts with Methyl-CpG-binding Protein 2 (MBD2) and Components of the NuRD Complex," J.Biol.Chem, Dec. 2004, vol. 279, No. 50, pp. 52456-52464.*
Ballestar et al., "Methyl-CpG binding proteins identify novel sites of epigenetic inactivation in human cancer," EMBO journal, 2003, vol. 22, No. 23, pp. 6335-6345.*
Yan et al., "Use of CpG island microarrays to identify colorectal tumors with a high degree of concurrent methylation," Methods, 2002, vol. 27, pp. 162-169.*
Cross, S., et al, "Purification of CpG Islands Using a Methylated DNA Binding Column," *Nature Genetics*, vol. 6, Mar. 1994, pp. 236-244, 1994 Nature Publishing Group; Institute of Cell and Molecular Biology, University of Edinburgh, Kings Buildings, Edinburgh, Scotland, UK.
Shiraishi, M., et al, "Isolation of DNA Fragments Associated With Methylated CpG Islands in Human Adenocarcinomas of the Lung Using a Methylated DNA Binding Column and Denaturing Gradient Gel Electrophoresis," *Proceedings of National Academy of Sciences*, USA, vol. 96, pp. 2913-2918, Mar. 1999 Genetics.
Jiang, C., et al, "MBD3L1 Is a Transcriptional Repressor That Interacts With Methyl-CpG-Binding Protein 2 (MBD2) and Components of the NuRD Complex," *The Journal of Biological Chemistry*, 2004 by The American Society for Biochemistry and Molecular Biology, Inc., vol. 279, No. 50, issue of Dec. 10, pp. 52456-52464, 2004, USA.
Rauch T., et al, "Methylated-CpG Island Recovery Assay: A New Technique for the Rapid Detection of Methylated-CpG Islands in Cancer," *Laboratory Investigation 2005*, vol. 85, pp. 1172-1180, 2005 USCAP, Inc.; Division of Biology, Beckman Research Institute of the City of Hope, Duarte, CA, USA.
Hendrich B., et al, "Mammalian Methyltransferases and Methyl-CpG-Binding Domains: Proteins Involved in DNA Methylation," Mol. and Cell. Biol., 1998, pp. 6538-6547.
Wade, P., "Methyl CpG Binding Proteins: Coupling Chromatin Architecture to Gene Regulation," *Oncogene* (2001), vol. 20, pp. 3166-3173, 2001 Nature Publishing Group; Emory University School of Medicine, Department of Pathology and Laboratory Medicine, Woodruff Memorial Research Building, Atlanta, Georgia, USA.
Hendrich, B. et al, "Identification and Characterization of a Family of Mammalian Methyl-CpG Binding Proteins," *Molecular and Cellular Biology*, Nov. 1998, pp. 6538-6547, 1998 American Society for Microbiology; Institute of Cell and Molecular Biology, University of Edinburgh, Edinburgh, Scotland.
Costello, J., et al, "Aberrant CpG-Island Methylation has Non-Random and Tumour-Type-Specific Patterns," *Nature Genetics*, vol. 25, Feb. 2000, pp. 132-138, 2000 Nature America Inc., USA.
Fraga, M. et al, "DNA Methylation: A Profile of Methods and Applications," *BioTechniques*, vol. 33, No. 3, pp. 632-649 (Sep. 2002); Spanish National Cancer Research Center (CNIO), Madrid, Spain.
Shiraishi, M., et al, "An Overview of the Analysis of DNA Methylation in Mammalian Genomes," *Biol. Chem.*, vol. 383, pp. 893-906, Jun. 2002; DNA Methylation and Genome Function Project, National Cancer Center Research Institute, Tokyo, Japan.
Pfeifer, G., et al, "Genomic Sequencing and Methylation Analysis by Ligation Mediated PCR," *Science*, vol. 246, Nov. 10, 1989, pp. 810-813; Molecular Biology Section, Beckman Research Institute of the City of Hope, Duarte, CA; California Institute of Technology, Division of Biology, Pasadena, CA.

(Continued)

*Primary Examiner*—Kenneth R. Horlick
*Assistant Examiner*—Molly Baughman
(74) *Attorney, Agent, or Firm*—Rothwell, Figg, Ernst & Manbeck P.C.

(57) ABSTRACT

The present invention provides new and improved assay for detection of genomic methylated CpG islands. This new method is termed the methylated-CpG island recovery assay (MIRA). In accordance with one embodiment, MIRA comprises the steps of: (a) incubating genomic DNA fragments with a methylated CpG island binding protein in the presence of a binding partner for the binding protein to produce bound DNA containing methylated CpG islands, (b) isolating the bound DNA, and (c) detecting CpG island methylation by gene-specific amplification reactions. In accordance with a preferred embodiment, MIRA comprises the steps of: (a) incubating sonicated genomic DNA with a matrix containing a fusion protein of glutathione S-transferase (GST) and MBD2b (GST-MBD2b) in the presence of MBD3L1 to produce bound DNA containing methylated CpG islands, (b) eluting bound DNA from the matrix, and (c) detecting CpG island methylation by gene-specific amplification reactions.

38 Claims, 10 Drawing Sheets

OTHER PUBLICATIONS

Clark, S. et al, "High Sensitivity Mapping of Methylated Cytosines," *Nucleic Acids Research*, 1994, vol. 22, No. 15, pp. 2990-2997; Kanematsu Laboratories, Royal Prince Alfred Hospital, Sydney, Australia; CSIRO Division of Biomolecular Engineering, Sydney Laboratory, Sydney, Australia; School of Biological Sciences, A12, University of Sydney, Australia.

Frommer, M., et al, "A Genomic Sequencing Protocol That Yields a Positive Display of 5-Methylcytosine Residues in Individual DNA Strands," *Proceedings of National Academy of Sciences*, USA, vol. 89, pp. 1827-1831, Mar. 1992, Genetics; The Kanematsu Laboratories, Royal Prince Alfred Hospital, Sydney, Australia; Division of Biomolecular Engineering, Laboratory for Molecular Biology, Commonwealth Scientific and Industrial Research Organization, Australia.

Xiong, Z., et al, "COBRA: A Sensitive and Quantitative DNA Methylation Assay," *Nucleic Acids Research*, 1997, vol. 25, No. 12, pp. 2532-2534, 1997 Oxford University Press; Department of Surgery and Department of Biochemistry and Molecular Biology, University of Southern California School of Medicine, The Norris Comprehensive Cancer Center, Los Angeles, California, USA.

Herman, J., et al, "Methylation-Specific PCR: A Novel PCR Assay for Methylation Status of CpG Islands," *Proceedings of National Academy of Sciencies*, USA, vol. 93, pp. 9821-9826, Sep. 1996, Medical Sciences; Oncology Center and Department of Medicine, The Johns Hopkins Medical Institutions, Baltimore, Maryland.

\* cited by examiner

Figure 2
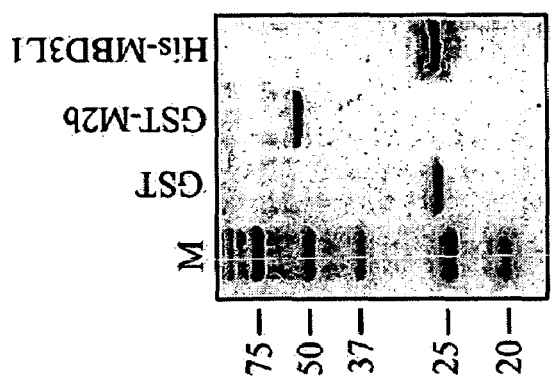
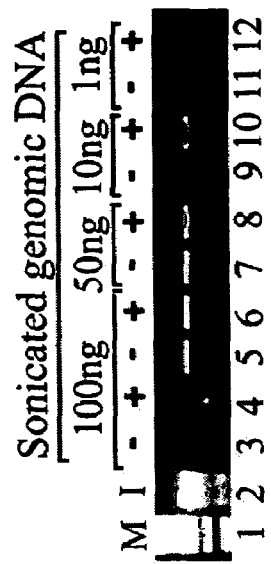
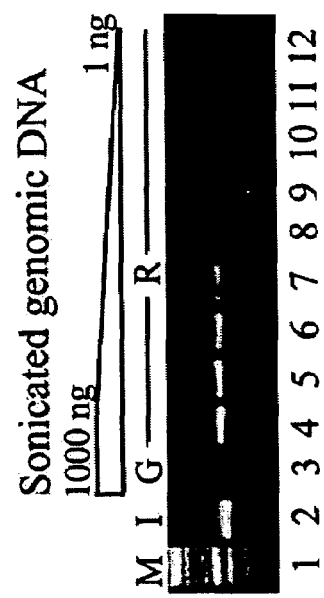

Figure 6

RASSF1A promoter

GCCAAGTGTGTTGCTTCAGCAAACCGGACCAGGAGGGCCAGGGCCGGATGTGGGACCC
TCTTCCTCTAGCACACAGTAAAGCTGGCCTCCAGAAACACGGGTATCTCCGTGGTGCTT
TGCGGTCGCCGTCGTTGTGCCGTCCGGGGTGGGGTGTGAGGAGGGGACGAAGGAGGGA
AGGAAGGGCAAGGGGGGGGGCTCTGCGAGAGCGCGCCCAGCCCCGCCTTCGGCCCC
ACAGTCCCTGCACCCAGTTTCCATTGCGCTCTCCTCAGCTCCTTCCCGCCGCCCA
GTCTGGATCCTGGGGAGGCGCTGAAGTCGGGCCGCCCTGTGCCCCGCCCGGCCCG
CGCTTGCTAGCGCCCAAAGCCAGCGAAGCACGGCCCAACGGGCCATGTCGGGGAGC
CTGAGCTCATTGAGCTGCGGG

There are 33 potential CpG dinucleotides for SssI and 5 for Hpa II methylation.

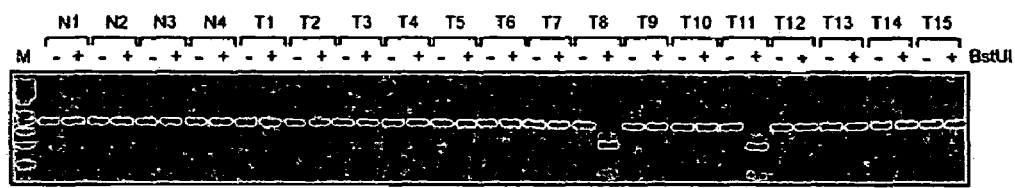
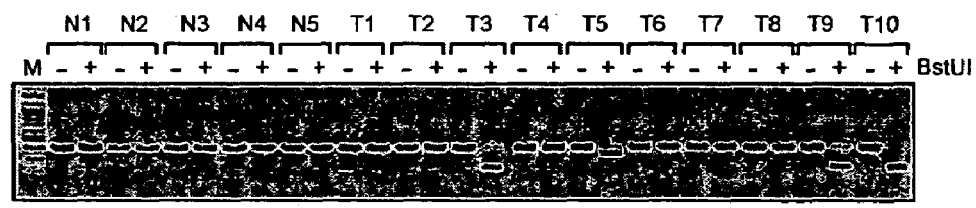
Figure 11
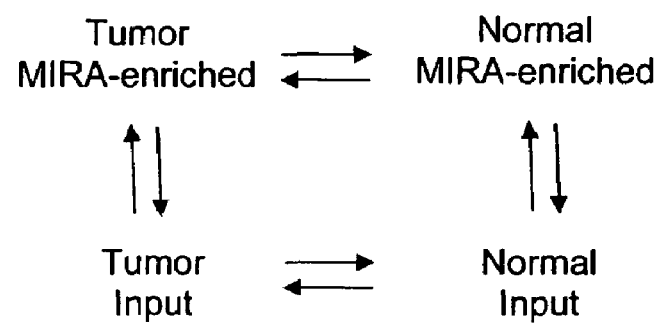
Figure 12

METHOD FOR DETECTING METHYLATED CPG ISLANDS

CROSS-REFERENCE TO RELATED APPLICATION

The present application is related to and claims priority under 35 U.S.C. § 119(e) to U.S. provisional patent application Ser. No. 60/668,572 filed on 6 Apr. 2005, incorporated herein by reference.

This application was made with Government support under Grant Nos. CA88873 and CA104967 funded by the National Institutes of Health, Bethesda, Md. The federal government may have certain rights in this invention.

BACKGROUND OF THE INVENTION

The present invention is directed to a method for detecting methylated CpG islands. The method exploits the presence of genomic DNA sequences that exhibit altered CpG methylation patterns in many diseases, including cancer. Thus, the method is useful in the diagnosis and prognosis of such diseases.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Methylation of DNA at CpG dinucleotides is one of the most important epigenetic modifications in mammalian cells. Short regions of DNA in which the frequency of 5'-CG-3' (CpG) dinucleotides are higher than in other regions of the genome are called CpG islands (Bird, 1986). CpG islands often harbor the promoters of genes and play a pivotal role in the control of gene expression. In normal tissue, CpG islands are usually unmethylated but a subset of islands becomes methylated during tumor development (Jones and Baylin, 2002; Costello et al., 2000; Esteller et al., 2001). Methyl-CpG binding domain (MBD) proteins specifically recognize methylated DNA sequences and are essential components of regulatory complexes that mediate transcriptional repression of methylated DNA (Hendrich and Bird, 2000; Wade, 2001). One of the best-characterized members of the MBD protein family is MBD2. MBD2 has two isoforms, MBD2a and MBD2b, which are alternatively translated from the same mRNA (Hendrich and Bird, 1998). Recent studies indicate that interacting proteins can modulate the methylated DNA-binding ability of the MBD2 protein (Jiang et al., 2004). MBD3L1 interacts with MBD2b in vivo and in vitro and promotes the formation of larger methylated-DNA binding complexes (Jiang et al., 2004).

In order to identify and characterize the chromosomal regions (particularly CpG islands) that undergo de novo methyation in tumorigenesis many technical approaches have been used (Costello et al., 2000; Fraga and Esteller, 2002; Shiraishi et al., 2002a). These methods can be classified into several groups on the basis of their principles. The first group of techniques is based on restriction endonuclease cleavage. These techniques require the presence of methylated cytosine residues at the recognition sequence that affect the cleavage activity of isoschizomeric restriction endonucleases (e.g., HpaII and MspI) (Singer et al., 1979). In this method the methylation sensitive and resistant enzyme pair produces characteristic fragment populations of the genomic DNA that can be detected by Southern blot hybridization. The technique is limited to specific restriction sites and requires large amounts of genomic DNA.

The second set of techniques makes use of the differential sensitivity of cytosine and 5-methylcytosine towards chemical modification and cleavage by employing Maxam-Gilbert sequencing technology (Maxam and Gilbert, 1980). The application of ligation-mediated PCR techniques to Maxam-Gilbert treated genomic DNA allows the exact identification and partial quantification of 5-methylcytosines at the single nucleotide level in mammalian genes (Pfeifer et al., 1989). Although highly specific and reasonably sensitive (requires 0.5 µg to 1 µg of DNA) these techniques are technically complex. The principle of bisulfite genomic sequencing is that methylated and unmethylated cytosine residues react in a different manner with sodium bisulfite (Clark et al., 1994; Frommer et al., 1992). After bisulfite treatment of genomic DNA, the unmethylated cytosines are converted to uracils by deamination, while methylated cytosine residues can hardly react with this agent and remain intact. After this chemical treatment the region of interest must be PCR amplified, and in most cases cloned and sequenced. Alignment analysis of the original (untreated) and cloned (treated) nucleotide sequences can reveal the in vivo methylation status of the amplified region. The PCR products obtained from bisulfite-treated DNA can also be further analyzed by combined bisulfite-restriction analysis (COBRA assay), which can distinguish between methylated and unmethylated DNA (Xiong and Laird, 1997).

Another commonly used sodium bilsulfite dependent technique is methylation-specific PCR (MSP) (Herman et al., 1996). Sodium bisulfite treated genomic DNA serves as the template for a subsequent PCR reaction. Specific sets of PCR primers are designed in such a way to discriminate between bisulfite modified and unmodified template DNA and between unmethylated (deaminated) and methylated (non-deaminated) cytosines at CpG sites. Another approach used for the identification of methylated CpG islands utilizes the ability of the MBD domain of the MeCP2 protein to selectively bind to methylated DNA sequences (Cross et al., 1994; Shiraishi et al., 1999). The bacterially expressed and purified His-tagged methyl-CpG binding domain is immobilized to a solid matrix and used for preparative column chromatography to isolate highly methylated DNA sequences. Restriction endonuclease digested genomic DNA is loaded onto the affinity column and methylated CpG island enriched fractions are eluted by a linear gradient of sodium chloride. PCR or Southern hybridization techniques are used to detect specific sequences in these fractions. There are several additional methods for analysis of methylation patterns but each of them is a derivative of the above-mentioned principles (Fraga and Esteller, 2002; Shiraishi et al., 2002a).

Most of the currently used methods for detecting methylated CpG islands, as described above, are based on sodium bisulfite conversion of genomic DNA followed by PCR reactions. In addition, most methods currently available are labor-intensive and use methylation-sensitive restriction endonucleases and thus are limited by the occurrence of the respective sites within the target sequence.

In addition to the above techniques, another way to find methylated genes is by using expression microarrays to identify genes reactivated by treatment with DNA methylation inhibitors, e.g. 5-aza-deoxycytidine (Shi et al., 2003; Suzuki et al., 2002; Yamashita et al., 2002). This approach can only be used with cell lines. Recently, genomic tiling and BAC microarrays have been introduced to map methylation patterns (Ching et al., 2005; Weber et al., 2005). These approaches are also limited, both in terms of their level of resolution and in terms of the requirements for restriction endonuclease recognition sites. An antibody against 5-methylcytosine has been used in immunoprecipitation experiments combined with microarrays (Weber et al., 2005; Keshet et al., 2006). However, this antibody requires single-stranded DNA for recognition, which is often difficult to achieve in CpG-rich regions.

In view of the above described disadvantages, it is desired to develop a methylation assay that does not depend on the use of sodium bisulfite but has similar sensitivity and specificity as bisulfite-based approaches and is less laborious. Such a methylation assay would be clinically useful in the early detection and diagnosis of any DNA methylation related disease, including cancer. It is also desired to adapt this methylation assay to microarray analysis for the determination of genome-wide DNA methylation patterns.

SUMMARY OF THE INVENTION

The present invention is directed to a method for detecting methylated CpG islands. The method exploits the presence of genomic DNA sequences that exhibit altered CpG methylation patterns in many diseases, including cancer. Thus, the method is useful in the diagnosis and prognosis of such diseases. Detection of methylated CpG islands in easily accessible biological materials such as serum is useful for the early diagnosis of disease and cancer. The present invention is also directed to the application of this method for microarray analysis to determine genome-wide DNA methylation patterns.

Thus, in one aspect, the present invention provides new and improved assay for detection of genomic methylated CpG islands. This new method is termed the methylated-CpG island recovery assay (MIRA). In accordance with one embodiment, MIRA comprises the steps of: (a) incubating genomic DNA fragments with a methylated CpG island binding protein in the presence of a binding partner for the binding protein to produce bound DNA containing methylated CpG islands, (b) isolating the bound DNA, and (c) detecting CpG island methylation by gene-specific amplification reactions. In accordance with a preferred embodiment, MIRA comprises the steps of: (a) incubating sonicated genomic DNA with a matrix containing a fusion protein of glutathione S-transferase (GST) and MBD2b (GST-MBD2b) in the presence of MBD3L1 to produce bound DNA containing methylated CpG islands, (b) eluting bound DNA from the matrix, and (c) detecting CpG island methylation by gene-specific amplification reactions.

In a second aspect, the present invention provides a method for the determination of genome-wide DNA methylation patterns by MIRA-assisted microarray analysis. This method, which is based on the methylated-CpG island recovery assay (MIRA), makes use of the high affinity of the MBD2b/MBD3L1 complex for methylated DNA (Jiang et al., 2004; Rauch and Pfeifer, 2005) and can be used to analyze the DNA methylation status of a large number of genes simultaneously using a microarray approach. The method comprises the steps of: (a) incubating genomic DNA fragments with a methylated CpG island binding protein in the presence of a binding partner for the binding protein to produce bound DNA containing methylated CpG islands, (b) isolating the bound DNA, (c) amplifying the bound DNA to produce MIRA-enriched fractions, (d) labeling input and MIRA-enriched fractions with different labels, such as fluorescent dyes, (e) mixing the labeled input and MIRA-enriched fractions, and (f) hybridizing the mixture to CpG island microarrays containing 12,192 CpG islands, of which 68% map to the 5' promoter sequences of genes (Cross et al., 1994; Heisler et al., 2005).

In a third aspect, the present invention provides a method for diagnosing an individual with a condition that is characterized by a level and/or pattern of methylated genomic CpG islands distinct from the level and/or pattern of methylated genomic CpG islands exhibited in the absence of the particular condition.

In a fourth aspect, the present invention provides a method for predicting the susceptibility of an individual to a condition that is characterized by a level and/or pattern of methylated genomic CpG islands that is distinct from the level and/or pattern of methylated genomic CpG islands exhibited in the absence of the condition.

BRIEF DESCRIPTION OF THE FIGURES

FIGS. 2A-2C show the determination of the sensitivity of MIRA. FIG. 2A: Purified proteins used in the assay are separated on a 13% SDS polyacrylamide gel. FIG. 2B: Decreasing amounts of sonicated genomic DNA (1 µg, 0.5 µg, 0.25 µg, 0.125 µg, 0.062 µg, 0.031 µg, 0.025 µg, 0.01 µg and 0.001 µg) isolated from A549 cells were incubated with GST-fused MBD2b protein. "I" represents the input genomic DNA and "R" stands for the recovered samples. In the negative control reaction, GST protein only ("G") was incubated with 1 µg of sonicated DNA. PCR was performed with primers specific for the RASSF1A promoter. FIG. 2C: The assay was performed both in the absence (−) and in the presence (+) of MBD3L1 protein. "I" stands for input DNA. Lanes 3 and 4, GST protein only; lanes 5-12, GST-MBD2b.

FIGS. 4A and 4B: $10^4$ cells from different cell lines were used as a starting material in these assays. "G" and "R" refers to GST only and GST-tagged MBD2b recovered samples, respectively. "I" stands for input DNA. "L" stands for LINE element specific control. FIG. 4C: 15 ng of sonicated blood (B) or pancreatic tumor (T) DNA served as templates for MIRA analysis.

FIG. 5A shows the binding capacity of the MIRA matrix. The assay was performed on a constant amount of sonicated A549 and HeLa genomic DNA and methylation-specific PCR was used to detect the methylation specific signal. Lane 1, 500 ng of A549 DNA; lane 2, 375 ng A549 DNA and 125 ng of HeLa DNA; lane 3, 250 ng A549 DNA and 250 ng of HeLa DNA; lane 4, 125 ng A549 DNA and 375 ng of HeLa DNA; lane 5, 500 ng of HeLa DNA. FIG. 5B shows the results of Bisulfite sequencing. After performing MIRA, the DNA was isolated from the supernatant and the pellet fractions of a 1:1 mix of A549 and HeLa DNA (500 ng total), treated with sodium bisulfite, and subjected to PCR amplification with primers that target the RASSF1A promoter and have the capacity to amplify both methylated and unmethylated molecules. The amplified products were cloned and 10 clones each were sequenced. Open and filled squares indicate unmethylated and methylated CpG dinucleotides, respectively.

FIG. 6 shows the effect of methylation density on MIRA's sensitivity. M.HpaII- and M.SssI-methylated RASSF1A promoter fragments were used as templates in MIRA and the methylation-specific signal was detected after 20 (lane 3), 25 (lane 4) and 30 (lanes 1, 2, and 5) cycles of PCR. "I", "G" and "MBD2b" refers to input, GST only and GST-tagged MBD2b recovered samples, respectively. The sequence for the RASSF1A promoter is set forth in SEQ ID NO: 1.

FIG. 9A: Efficiency of the MIRA pull-down. Restriction-cut human genomic DNA was methylated with different DNA methylases (SssI, HpaII and/or HhaI) to introduce different numbers of methylated CpGs into the unmethylated CpG island promoter of the TBP gene. After MIRA, the fragments were amplified by quantitative real-time PCR using TBP-specific primers. FIG. 9B: Schematic diagram of the method. MIRA-enriched DNA can be cell-specifically labeled with Cy3 and Cy5 fluorescence dyes, mixed and hybridized to CpG island microarrays. Input and MIRA-enriched fractions are labeled with different dyes, mixed, and hybridized to the slides and the relative enrichment factors between different cell types and tissues are determined. For confirmation, MIRA-enriched DNA from normal and tumor cells can be mixed and hybridized directly. FIG. 9C: Representative data for MIRA microarrays. In the left and middle panels, the MIRA-enriched fractions were labeled red and the input fractions green, and in the right panels, the MIRA-enriched A549 DNA was labeled green and the NHBE cell DNA was labeled red. FIG. 9D: Pair-wise comparison. Enrichment factors obtained from normal human bronchial epithelial (NHBE) cells (vertical axis) and A549 cells (horizontal axis) were compared. The dots in the blue circle are the targets selectively methylated in tumor cell DNA.

FIG. 10A: Confirmation of tumor cell specific methylation of four candidate target genes identified by the MIRA-assisted microarray approach (Targets 1, 4, 10, and 20 in Table 1). A549 and NHBE cell DNA was treated with sodium bisulfite and the target CpG island sequences were amplified using specific primers. Methylation was confirmed by a BstUI COBRA assay producing cleavage products (arrows) when methylation at 5'-CGCG sequences is present. FIG. 10B: Methylation of the DLEC1 gene in primary lung cancers. DNA was isolated from primary NSCLC tumors (T) and their adjacent normal tissues (N). After sodium bisulfite treatment, the DLEC1 promoter CpG island was PCR amplified. Cutting with BstUI indicates methylation of 5'-CGCG sequences within this CpG island sequence, which contains 3 BstUI sites (see samples # T4, T6, T8, T9, T10, and T15). FIG. 10C: Determination of tumor cell-specific methylation of the CpG island of the DLEC1 gene by bisulfite sequencing. Bisulfite genomic sequencing was performed on DNA isolated from A549 cells, NHBE cells, a primary lung tumor and adjacent normal lung tissue. Primers specific for the DLEC1 CpG island (gray shading) were used. Sequencing results of several independent clones are shown. Methylated CpG dinucleotides are shown as black squares.

FIGS. 11A-11B show methylation of the DLEC1 gene in primary esophageal cancers and melanomas. DNA was isolated from 15 primary esophageal cancers and 10 melanomas (T=tumor) and adjacent normal tissues (N=normal). After sodium bisulfite treatment, the DLEC1 promoter CpG island was PCR amplified. Cutting with BstUI indicates methylation of 5'-CGCG sequences within this CpG island sequence, which contains 3 BstUI sites (methylation is present in samples # T1, T8, and T11 of the esophageal cancers and in samples T3, T9, and T10 of the melanomas). FIG. 11A: Esophageal cancers. FIG. 11B: Melanomas.

FIG. 12 shows the experimental design of MIRA CpG island arrays. Two independent MIRA assays were performed for tumor and normal tissue, and the input and MIRA-enriched fractions were labeled using either Cy3 or Cy5. Each arrow represents one array/hybridization. The samples the arrows are pointing to were labeled with Cy5 and the samples at the other end of the arrow were labeled with Cy3. A total of eight arrays were labeled as dye-swap pairs.

DETAILED DESCRIPTION OF THE INVENTION

Figure 1:
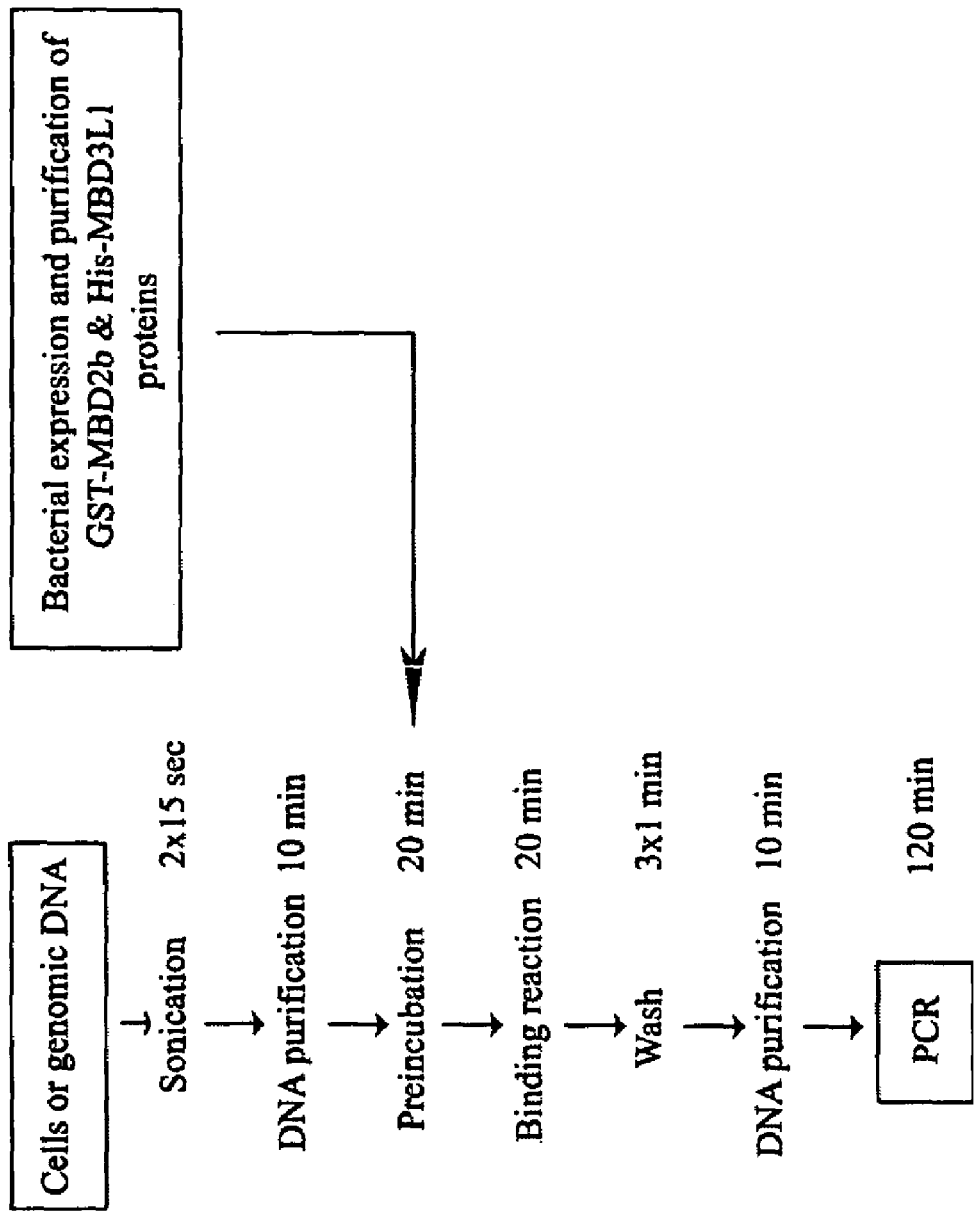
FIG. 1 shows a schematic diagram of the methylated-CpG island recovery assay (MIRA).

The present invention is directed to a method for detecting methylated CpG islands. The method exploits the presence of genomic DNA sequences that exhibit altered CpG methylation patterns in many diseases, including cancer. Thus, the method is useful in the diagnosis and prognosis of such diseases. Detection of methylated CpG islands in easily accessible biological materials such as serum is useful for the early diagnosis of disease and cancer. As used herein, the term "cancer" is intended to mean a class of diseases characterized by the uncontrolled growth of aberrant cells, including all known cancers, and neoplastic conditions, whether characterized as malignant, benign, soft tissue or solid tumor.

Thus, the present invention provides new and improved assay for detection of methylated CpG islands. This new method is termed the methylated-CpG island recovery assay (MIRA). In accordance with one embodiment, MIRA comprises the steps of: (a) incubating genomic DNA fragments with a methylated CpG island binding protein in the presence of a binding partner for the binding protein to produce bound DNA containing methylated CpG islands, (b) isolating bound DNA, and (c) detecting CpG island methylation by gene-specific amplification reactions.

In accordance with a second embodiment, MIRA comprises the steps of: (a) incubating genomic DNA fragments with a solid phase containing a methylated CpG island binding protein in the presence of a binding partner for the binding protein to produce bound DNA containing methylated CpG islands, (b) eluting bound DNA from the solid phase, and (c) detecting CpG island methylation by gene-specific amplification reactions.

In accordance with a preferred embodiment, MIRA comprises the steps of: (a) incubating sonicated genomic DNA isolated from cells or tissue with a matrix containing a fusion protein of glutathione S-transferase (GST) and MBD2b (GST-MBD2b) in the presence of MBD3L1 to produce bound DNA containing methylated CpG islands, (b) eluting bound DNA from the matrix, and (c) detecting CpG island methylation by gene-specific amplification reactions. MIRA is a specific and sensitive but not laborious technique that can be clinically useful in the detection and diagnosis of any DNA methylation associated disease including cancer.

In accordance with the present invention, the first step comprises incubating genomic DNA with a methylated CpG island binding protein in the presence of a binding partner of the binding protein. This incubation results in bound DNA that contains methylated CpG islands. The genomic DNA is isolated from a sample and is preferably treated to produce genomic DNA fragments. Any technique that will fragment the genomic DNA can be used in this aspect of the invention. For example, the genomic DNA can be digested with restriction endonucleases that do not cleave methylated CpG islands or can be treated with chemical agents as are well known in the art. It is preferred that the genomic DNA be fragmented by sonication. Any sonication procedure known in the art can be used to produce genomic DNA fragments.

As used herein, the term "sample" is intended to mean any biological fluid, cell, tissue, organ or portion thereof, that contains genomic DNA suitable for methylation detection using MIRA. A test sample can include or be suspected to include a neoplastic cell, such as a cell from the colon, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. A reference sample can be used to establish a reference level and, accordingly, can be derived from the source tissue that meets having the particular phenotypic characteristics to which the test sample is to be compared.

A sample may be obtained in a variety of ways known in the art. Samples may be obtained according to standard techniques from all types of biological sources that are usual sources of genomic DNA including, but not limited to cells or cellular components which contain DNA, cell lines, biopsies, bodily fluids such as blood, sputum, stool, urine, cerebrospinal fluid, ejaculate, tissue embedded in paraffin such as tissue from eyes, intestine, kidney, brain, heart, prostate, lung, breast or liver, histological object slides, and all possible combinations thereof. A suitable biological sample can be sourced and acquired subsequent to the formulation of the diagnostic aim of the marker. A sample can be derived from a population of cells or from a tissue that is predicted to be afflicted with or phenotypic of the condition. The genomic DNA can be derived from a high-quality source such that the sample contains only the tissue type of interest, minimum contamination and minimum DNA fragmentation. In particular, samples should be representative of the tissue or cell type of interest that is to be handled by the diagnostic assay. It is understood that samples can be analyzed individually or pooled depending on the purpose of the user. In addition, a population or set of samples from an individual source can be analyzed to maximize confidence in the results and can be a sample set size of 10, 15, 20, 25, 50, 75, 100, 150 or sample set sizes in the hundreds.

The methylated CpG island binding protein may be any protein that is capable of binding genomic DNA containing methylated CpG islands. Examples of such binding proteins include, but are not limited to, MBD2b, MBD2a, MBD3, MBD4, MBD1 and MeCP2. In the preferred embodiment, the binding protein is MBD2b. The binding partner that is utilized in the present invention is selected on the basis of the binding protein that is used. Examples of binding partners for the above binding proteins include, but are not limited to, MBD3L1 and MBD3L2. In the preferred embodiment, the binding partner is MBD3L1. In the description that follows, reference will be made to MBD2b as the binding protein and MBD3L1 as the binding partner. However, it is to be understood that any of the other binding proteins and binding partners can be used in place of the MBD2b and MBD3L1.

The binding protein, e.g., MBD2b, is preferably attached to a matrix using techniques well known in the art, although it is not necessary for all embodiments of the invention. In one embodiment, the binding protein, e.g., MBD2b, is used as a fusion protein of GST such that the GST is the N-terminus of the fusion protein and the binding protein, e.g., MBD2b, is the C-terminus. In this embodiment, the matrix is a glutathione Sepharose CL-4B matrix. The incubation of the sonicated genomic DNA and the GST-tagged binding protein, e.g., MBD2b, bound to the matrix is performed in a binding reaction mixture. In one embodiment, the reaction mixture comprises 10 mM Tris-HCl, pH 7.5, 50 mM NaCl, 1 mM EDTA, 1 mM DTT, 3 mM $MgCl_2$, 0.1% Triton-X100, 5% glycerol, and 25 µg/ml BSA. Other binding reaction mixtures well known to skilled artisans can be used in place of this reaction mixture. The incubation is performed for a sufficient length of time so that genomic DNA containing methylated CpG islands binds to the binding protein, e.g., MBD2b. A typical incubation time is 20 min at 4° C., although other times and temperatures can be used. In the preferred embodiment, the binding reaction is conducted in the presence of a binding partner, e.g., MBD3L1, of the binding protein, e.g., MBD2b. In this embodiment, the binding partner, e.g., MBD3L1, preferably as a His-tagged binding partner, e.g., MBD3L1, is pre-incubated with the binding protein, e.g., MBD2b, preferably as a GST-MBD2b matrix, prior to the incubation with the sonicated genomic DNA. A typical pre-incubation time is 20 min at 4° C., although other times and temperatures can be used. An excess of the binding partner, e.g., MBD3L1, is used for the pre-incubation step.

In the second step, the bound DNA is separated from the methylated CpG island binding protein. In a preferred embodiment, the bound DNA is eluted from the matrix after the matrix has been washed to remove unbound DNA. In the preferred embodiment in which a glutathione Sepharose CL-4B matrix is used, the methylated DNA enriched genomic DNA fraction is eluted by the addition of a guanidinium hydrochloride containing buffer. This fraction is preferably purified before further use.

In the third step, CpG island methylation is detected by gene-specific amplification reactions. In accordance with the present invention, the first step results in an enrichment and not a purification of methylated CpG islands that are bound by the methylated CpG binding protein. As a result, it is preferred that the amplification be performed and stopped during the linear stage of amplification. The gene specific amplification is performed using primers or other amplification components that are specific for known methylated CpG island sequences known to be associated with disease or cancer, including those described herein. A variety of amplification techniques may be used for this gene-specific amplification. Some of these techniques may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al. (1991); Eckert and Kunkel (1991); *PCR* (Eds. McPherson et al., IRL Press, Oxford); and U.S. Pat. Nos. 4,683,202, 4,683, 195, 4,800,159 4,965,188, and 5,333,675, each of which is incorporated herein by reference.

Other suitable amplification methods include the ligase chain reaction (LCR) (Wu and Wallace, 1989; Landegren et al., 1988; Barringer et al., 1990), transcription amplification (Kwoh et al., 1989; WO 88/10315), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), self-sustained sequence replication (Guatelli et al., 1990; WO 90/06995) and nucleic acid based sequence amplification (NABSA) (U.S. Pat. Nos. 5,409,818, 5,554,517, and 6,063,603), nick displacement amplification (NDA) (U.S. published patent application Nos. 2003/0138800 A1 and 2003/0082590 A1; WO 2004/067726; WO 03/008642), each reference of which is incorporated herein by reference. Other amplification methods that may be used are described in, U.S. Pat. Nos. 5,242,794, 5,494,810 and 4,988,617, each of which is incorporated herein by reference. In the preferred embodiment, PCR is used for the gene-specific amplifications.

The DNA may be amplified on an array. See, for example, U.S. Pat. No. 6,300,070, incorporated herein by reference. Alternatively, the DNA may be amplified using high-throughput techniques, such as those described further below. The use of an array or high-throughput techniques for DNA amplification enable the detection of multiple methylated CpG islands. Multiplexing can also be accomplished by using differentially labeled primers and by designing amplification products that can be size distinguished, such as by gel electrophoresis.

Thus, amplified products are detected using conventional techniques. In one embodiment, amplified products are separated by agarose gel electrophoresis and then detected by conventional techniques. Alternatively, labeled primers can be used in the amplification reaction. If DNA amplification is performed on an array or using high-throughput techniques, then each individual sample can be separately analyzed for the presence of an amplified product. The presence of an amplified product detects the presence of specific methylated CpG islands, based on the primers that are used in the amplification reactions.

Of particular interest is the combination of MIRA and MSP for biological samples in which the methylated CpG island(s) represent only a very small fraction of the total CpG island sequences, such as blood, serum, sputum, urine, or other biological fluids or tissue samples. In this case MIRA can be used to enrich the fraction containing methylated CpG islands. MSP is then used for the detection of specific methylated CpG island sequences. In accordance with MSP, the MIRA-enriched DNA is treated with sodium bisulfite or a comparable agent which modifies all unmethylated but not methylated cytosines, e.g., an agent which converts all unmethylated but not methylated cytosines to uracil. The treated MIRA-enriched DNA is then subsequently amplificied with primers specific for methylated versus unmethylated DNA. Further details of MSP is described in U.S. Pat. Nos. 5,786,146, 6,017,704, 6,200,756 and 6,265,171, each incorporated herein by reference.

Figure 8:
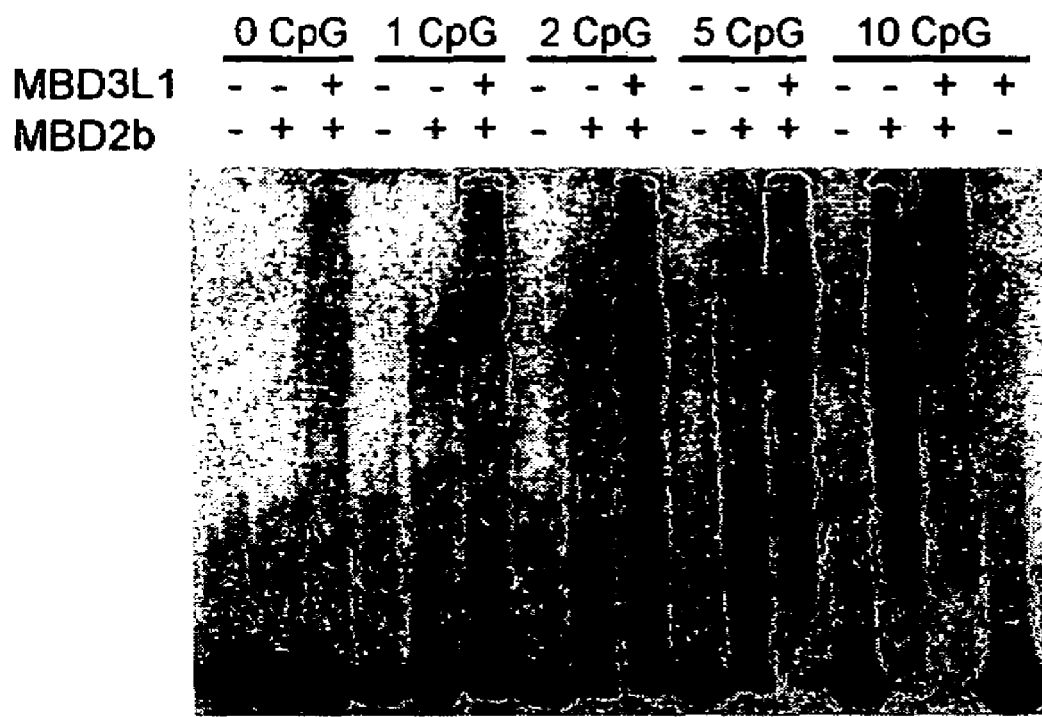
FIG. 8 shows that the MBD2b/MBD3L1 complex has a much higher affinity for methylated DNA than MBD2b alone. A 55-mer oligonucleotide containing varying numbers of symmetrically methylated CpG dinucleotides was incubated with recombinant MBD2b alone (100 ng of protein) or with the MBD2b/MBD3L1 complex (100 ng of each protein). The protein DNA complexes were incubated for 5 min at room temperature in buffer containing 10 mM Tris-HCl, pH 7.5, 50 mM NaCl, 1 mM EDTA, 1 mM DTT, 3 mM $MgCl_2$, 0.1% Triton-X100, 5% glycerol, 25 µg/ml BSA and 1.25 µg/ml sonicated JM110 (dcm minus) DNA. A mobility shift assay was performed using a 5% polyacrylamide gel.
Figure 9:
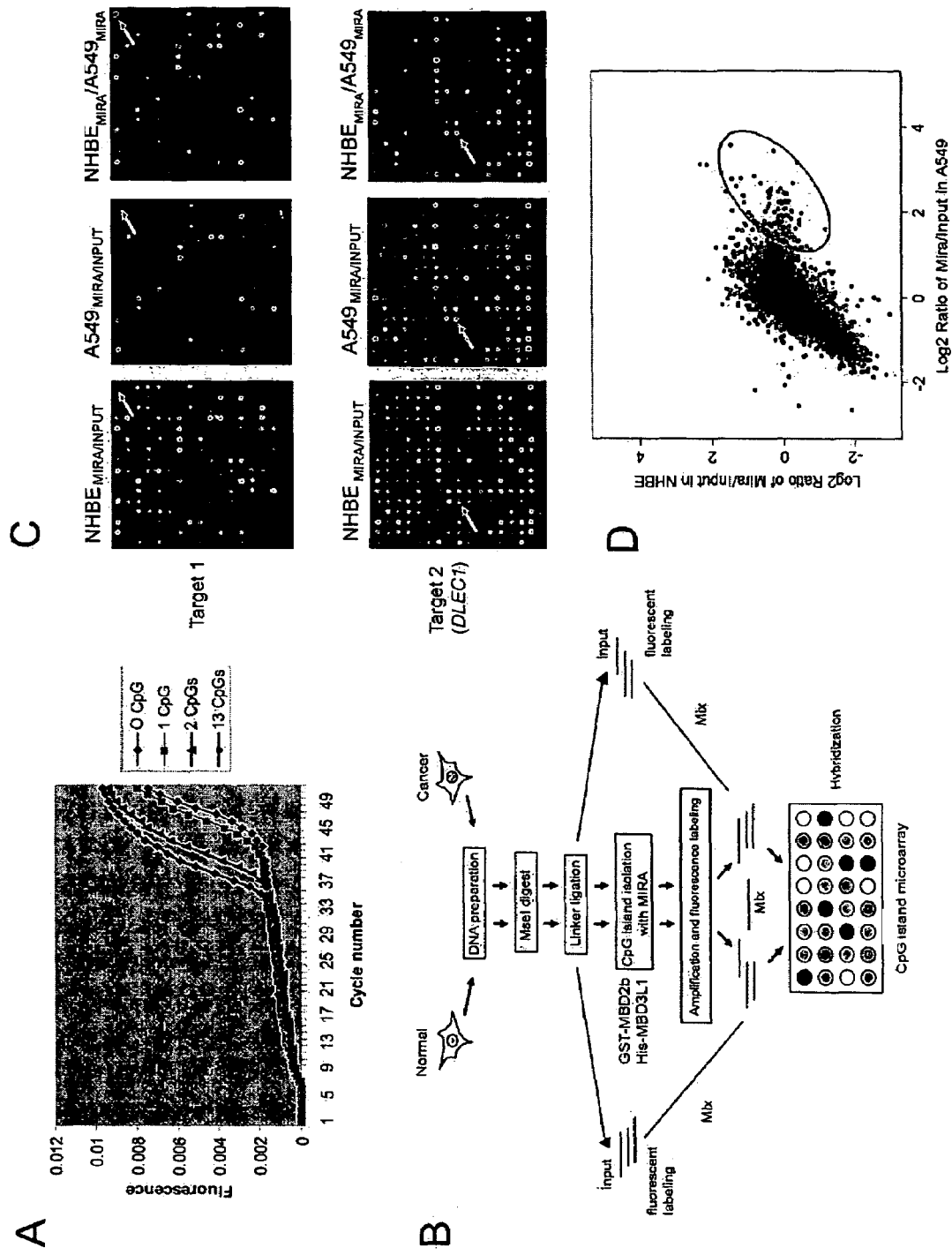
FIGS. 9A-9D show MIRA-assisted CpG island microarray analysis.

The methyl-CpG binding protein MBD2b has a high affinity for methylated DNA and recognizes a wide range of methylated CpG sequences (Fraga et al., 2003), unlike MeCP2, which prefers AT-rich neighboring sequence contexts (Klose et al., 2005). Data in FIG. 8 confirm that the MBD2b/MBD3L1 complex has a much higher affinity for methylated DNA than MBD2b alone. MIRA has a high specificity for enriching methylated DNA and unmethylated DNA fragments stay in the supernatant (Rauch and Pfeifer, 2005). It was initially determined that the pull-down of methylated DNA by MIRA is dependent on the number of methylated CpGs present in genomic DNA fragments. Recovery of fragments containing 13 methylated CpGs was more efficient than recovery of fragments containing only two CpGs and much more efficient than recovery of fragments with only one or zero methylated CpG sites (FIG. 9A). Thus, the efficiency of the MIRA enrichment depends on CpG density and the approach appears to be ideally suited for pulling down methylated CpG islands.

Also of particular interest is the application of MIRA to microarray analysis for the determination of genome-wide DNA methylation patterns. FIG. 1B outlines one embodiment of the MIRA microarray approach. Genomic DNA, isolated from different sources, is cleaved with a restriction enzyme, which produces small 200-300 bp fragments and cuts outside of CpG islands, and compatible linkers are ligated to the ends. One suitable restriction enzyme is MseI (5'TTAA), although a skilled artisan will readily know other restriction enzymes that meet the above requirements of size and cutting outside of CpG islands. Then the MIRA pulldown is performed to isolate the methylated DNA fraction. Input and MIRA-enriched fractions are labeled with different labels, such as fluorescent dyes, mixed, and hybridized to CpG island microarrays, such as microarrays containing 12,192 CpG islands, of which 68% map to the 5' promoter sequences of genes (Cross et al., 1994; Heisler et al., 2005). The microarrays can be of any format known in the art, such as DNA chips, beads, and the like. The input DNA can be DNA isolated from normal tissue, diseased tissue or both normal and disease tissue.

MIRA is particularly useful for diagnosing an individual with a condition that is characterized by a level and/or pattern of methylated genomic CpG islands distinct from the level and/or pattern of methylated genomic CpG islands exhibited in the absence of the particular condition. MIRA is also particularly useful for predicting the susceptibility of an individual to a condition that is characterized by a level and/or pattern of methylated genomic CpG islands that is distinct from the level and/or pattern of methylated genomic CpG islands exhibited in the absence of the condition.

With particular regard to cancer, changes in DNA methylation have been recognized as one of the most common molecular alternations in human neoplasia (see Baylin et al., 1998 and Schmutte and Jones 1998). Hypermethylation of CpG islands located in the promoter regions of tumor suppressor genes is a well-established and common mechanism for gene inactivation in cancer (Esteller, 2002). In contrast, a global hypomethylation of genomic DNA is observed in tumor cells; and a correlation between hypomethylation and increased gene expression has been reported for some oncogenes (Feinberg and Vogelstein, 1983; Hanada et al., 1993). Monitoring global changes in methylation pattern has been applied to molecular classification in breast cancer (Huang et al., 1999). In addition, many studies have identified a few specific methylation patterns in tumor suppressor genes, for example, p16, a cyclin-dependent kinase inhibitor, in certain human cancer types (Otterson et al., 1995; Herman et al., 1995). Some of the most recent examples include the discoveries of causal relationship between the loss of RUNX3 expression, due to hypermethylation, and gastric cancer (Li et al., 2002); loss of IGF2 imprinting in colorectal cancer (Cui et al., 2003); reduced Hic gene expression in several types of human cancer (Chen et al., 2003; Fujii et al., 1998; Kanai et al., 1999) and frequent RASSF1A promoter hypermethylation in many human tumors (Dammann et al., 2005). Other methylation patterns of genomic CpG islands and association with different types of cancers have been described in U.S. published patent application number 2005/0026183, incorporated herein by reference.

MIRA can also be used to identify differentially methylated genomic CpG islands associated with disease, including cancer, in an individual by obtaining a biological sample comprising genomic DNA from the individual, measuring the level of methylated genomic CpG islands associated with the disease in the sample, and comparing the level of methylated genomic CpG islands in the sample to a reference level of methylated genomic CpG samples. A difference in the level of methylation of said genomic CpG islands in the sample compared to the reference level identifies differentially methylated genomic CpG islands associated with a disease or cancer.

The level of methylation of the differentially methylated genomic CpG islands can provide a variety of information about the disease or cancer and can be used, for example, to diagnose a disease or cancer in the individual; to predict the course of the disease or cancer in the individual; to predict the susceptibility to disease or cancer in the individual, to stage the progression of the disease or cancer in the individual; to predict the likelihood of overall survival for the individual; to predict the likelihood of recurrence of disease or cancer for the individual; to determine the effectiveness of a treatment course undergone by the individual.

The level of methylation that is detected in a biological sample can be decreased or increased in comparison to the reference level and alterations that increase or decrease methylation can be detected and provide useful prognostic or diagnostic information. For example, hypermethylation of CpG islands located in the promoter regions of tumor suppressor genes have been established as common mechanisms for gene inactivation in cancers (Esteller, 2002). Thus, a detailed study of methylation pattern in selected, staged tumor samples compared to matched normal tissues from the same patient can identify unique molecular markers for cancer classification.

In addition to detecting levels of methylation, MIRA can also be used to detect patterns of methylation. It has been confirmed previously that neoplastic cells can exhibit unusual patterns of gene methylation (Feinberg and Vogelstein, 1983). Previous genetic studies of various conditions, for example, schizophrenia and bipolar disorder, seemed to implicate regions of particular chromosomes 22, but studies failed to identify a susceptibility gene. Analysis of methylation patterns across this chromosome in biological samples from afflicted individuals can reveal epigenetic changes in the form of altered levels of methylation of subsets of genomic CpG islands that make up a pattern of affected genomic targets that can be correlated with a condition.

MIRA can also be used for prognostic methods that are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside the affected organ that were not removed by surgery. These cancer cells, referred to as micrometastases, cannot typically be detected with currently available tests.

The prognostic methods can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

MIRA can also be used for methods for determining a prognosis for survival for a cancer patient. One such method involves (a) measuring a level of methylation for one or more of genes in a neoplastic cell-containing sample from the cancer patient, and (b) comparing the level of methylation in the sample to a reference level of methylation for the gene, wherein a low level of methylation for the gene in the sample correlates with increased survival of the patient.

MIRA can also be used with methods for monitoring the effectiveness of a course of treatment for a patient with cancer. One such method involves (a) determining a level of methylation of one or more of genes in a neoplastic cell containing sample from the cancer patient prior to treatment, and (b) determining the level of methylation for the gene in a neoplastic cell-containing sample from the patient after treatment, whereby comparison of the level of methylation for the gene prior to treatment with the level of methylation for the gene after treatment indicates the effectiveness of the treatment.

As used herein, the term "reference level" refers to a control level of expression of a marker used to evaluate a test level of expression of a biomarker in a neoplastic cell-containing sample of a patient. For example, when the level of methylation of one or more genes, referred to herein as "genomic targets," in the neoplastic cells of a patient are higher than the reference level of methylation for the genes, the cells are considered to have a low level of expression of the gene. Conversely, when the level of methylation of one or more genes in the neoplastic cells of a patient are lower than the reference level, the cells are considered to have a higher level of expression, of the gene.

A reference level can be determined based on reference samples collected from age-matched normal classes of adjacent tissues, and with normal peripheral blood lymphocytes. The reference level can be determined by any of a variety of methods, provided that the resulting reference level accurately provides a level of a marker above which exists a first group of patients having a different probability of survival than that of a second group of patients having levels of the biomarker below the reference level. The reference level can be determined by, for example, measuring the level of expression of a biomarker (herein the level of methylation of a gene) in non-tumorous cells from the same tissue as the tissue of the neoplastic cells to be tested. The reference level can also be a level of a biomarker of in vitro cultured cells which can be manipulated to simulate tumor cells, or can be manipulated in any other manner which yields expression levels which accurately determine the reference level. The reference level can also be determined by comparison of the level of a biomarker, such as methylation of one or more genes, in populations of patients having the same cancer. This can be accomplished, for example, by histogram analysis, in which an entire cohort of patients are graphically presented, wherein a first axis represents the level of the biomarker, and a second axis represents the number of patients in the cohort whose neoplastic cells express the biomarker at a given level.

Two or more separate groups of patients can be determined by identification of subset populations of the cohort which have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker. The reference level can be a single number, equally applicable to every patient, or the reference level can vary, according to specific subpopulations of patients. For example, older individuals might have a different reference level than younger individuals for the same cancer. In another example, the reference level might be a certain ratio of a biomarker in the neoplastic cells of a patient relative to the biomarker levels in non-tumor cells within the same patient. Thus the reference level for each patient can be proscribed by a reference ratio of one or more genomic markers, such as methylation of one or more genes, wherein the reference ratio can be determined by any of the methods for determining the reference levels known in the art.

It is understood that the reference level has to correspond to the level of methylated genomic CpG islands present in a corresponding sample that allows comparison to the desired phenotype. For example, in a diagnostic application a reference level can be based on a sample that is derived from a cancer-free origin so as to allow comparison to the biological test sample for purposes of diagnosis. In a method of staging a cancer it can be useful to apply in parallel a series of reference levels, each based on a sample that is derived from a cancer that has been classified based on parameters established in the art, for example, phenotypic or cytological characteristics, as representing a particular cancer stage so as to allow comparison to the biological test sample for purposes of staging. In addition, progression of the course of a condition can be determined by determining the rate of change in the level or pattern of methylation of genomic CpG islands by comparison to reference levels derived from reference samples that represent time points within an established progression rate. It is understood, that the user will be able to select the reference sample and establish the reference level based on the particular purpose of the comparison.

MIRA can also be applied to the characterization, classification, differentiation, grading, staging, diagnosis, or prognosis of a condition characterized by a pattern of methylated genomic CpG islands that is distinct from the pattern of methylated genomic CpG islands exhibited in the absence of the condition. A condition that is suitable can be, for example, cell proliferative disorder or predisposition to cell proliferative disorder; metabolic malfunction or disorder; immune malfunction, damage or disorder; CNS malfunction, damage or disease; symptoms of aggression or behavioral disturbance; clinical, psychological and social consequences of brain damage; psychotic disturbance and personality disorder; dementia or associated syndrome; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headache or sexual malfunction, and combinations thereof.

The use of MIRA makes available diagnostic and/or prognostic assays for the analysis of the methylation status of CpG islands as markers for disease or disease-related conditions. MIRA can be used with assays to provide a systematic method for the identification, assessment and validation of genomic targets as well as a systematic means for the identification and verification of multiple condition relevant CpG islands to be used alone, or in combination with other CpG islands, for example, as a panel or array of methylation patterns, that form the basis of a clinically relevant diagnostic or prognostic assay. MIRA can be used in these methods to enable differentiation between two or more phenotypically distinct classes of biological matter and allows for the comparative analysis of the methylation patterns of CpG islands within each of the classes.

MIRA lends itself for systematic study of CpG island methylation using microarray-based approaches. In one embodiment, genomic DNA is cleaved with the restriction endonuclease that cleaves outside of CpG islands prior to MIRA. One suitable restriction endonuclease is MseI (5'TTAA). After selective enrichment of the methylated CpG island fraction by MIRA, oligonucleotide linkers are ligated to the restriction endonuclease-cleaved genomic DNA. PCR using the linker oligonucleotides and fluorescent dye-labeled deoxynucleotides are used to amplify the methylated CpG island fraction. The amplified and dye-labeled DNA are used as a hybridization probe on CpG island-containing microarrays. By this means, a large number of methylated CpG islands can be monitored simultaneously.

MIRA can be used to provide assays for specific identification of methylation patterns in different cancer types and cancer stages. An advantage of MIRA is that it provides a high throughput methylation analysis system that can be commercialized, both through a service business—in which customers can provide samples and a gene list (CpG site list) for analysis in the methods—and through products that can be used in standard laboratory conditions.

A number of high throughput approaches to performing PCR and other amplification reactions have been developed, e.g., involving amplification reactions in microfluidic devices, as well as methods for detecting and analyzing amplified nucleic acids in or on the devices. Details regarding such technology is found in the technical and patent literature, e.g., Kopp et al. (1998); U.S. Pat. No. 6,444,461; U.S. Pat. Nos. 6,406,893, 6,391,622, 6,303,343, 6,171,850, 5,939,291, 5,955,029 and 5,965,410; U.S. published patent application Nos. 2005/0042639 A1 and 2004/0259237 A1, each incorporated herein by reference.

High throughput approaches use robotics for serial preparation and parallel processing of a large number of samples. The use of microcolumns in capturing the specific analytes enables an arrayed format that is ideal for such high-throughput processing since it minimizes the physical volume and/or area occupied by the microcolumn array. Affinity microcolumns can be used with appropriately configured robotics to allow multiple samples to be prepared, processed, start-to-finish, simultaneously on a unified platform thereby enabling high throughput of samples. Specifically, all capture, separation and elution steps can be performed within the microcolumns managed by the robotics system or systems. With the microcolumns, parallel-processing sequences can be used without disruption and the integrity of an ordered spatial array is maintained throughout the entire process. Most conveniently, multiple preparations/analyses are performed serially and in parallel using robotics fitted to commonly used spatial arrays, e.g., 4-, 8-, 16-, 48-, 96-, 384 or 1536 well microtiter plate formats. It is emphasized that the MIRA procedure does not involve any ethanol precipitation steps and, as such, is amenable to automation.

MIRA is useful for the identification of differentially methylated CpG islands within genomic DNA that are particularly informative with respect to disease states. These may be used either alone or as components of a gene panel in diagnostic and/or prognostic assays.

In particular embodiments, MIRA may be used for the prediction and diagnosis of conditions characterized by a pattern of methylated genomic CpG islands that is distinct from the pattern of methylated genomic CpG islands exhibited in the absence of the particular condition, for example, cell proliferative disorders, such as cancer; dysfunctions, damages or diseases of the central nervous system (CNS), including aggressive symptoms or behavioral disorders; clinical, psychological and social consequences of brain injuries; psychotic disorders and disorders of the personality, dementia and/or associates syndromes; cardiovascular diseases, malfunctions or damages; diseases, malfunctions or damages of the gastrointestine diseases; malfunctions or damages of the respiratory system; injury, inflammation, infection, immunity and/or reconvalescence, diseases; malfunctions or damages as consequences of modifications in the developmental process; diseases, malfunctions or damages of the skin, muscles, connective tissue or bones; endocrine or metabolic diseases malfunctions or damages; headache; and sexual malfunctions; or combinations thereof.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebra fish* (Danio rerio), (4th Ed., Univ. of Oregon Press, Eugene, 2000).

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Plasmid Constructs and Protein Expression

For the expression of GST-tagged recombinant MBD2b protein, the RT-PCR-generated full-length cDNA was cloned into the pGEX-5X-1 expression vector (Amersham Pharmacia Biotech). The His-tagged MBD3L1 protein expression vector was constructed as described earlier (Jiang et al., 2004). Expression constructs were transformed into *E. coli* BL21(DE) and expression was induced with 0.5 mM IPTG for 4 hours at 37° C. Bacterial pellets were resuspended in ice-cold STE buffer (10 mM Tris-HCl pH 7.8, 150 mM NaCl, 1 mM EDTA) containing 100 µg/ml lysozyme. After 10 min incubation on ice bacteria were lysed by addition of 1.5% of N-lauroylsarcosine (final concentration) and sonicated three times for 1 min. The lysate was cleared by centrifugation and Glutathione Sepharose 4B (Amersham Bioscience) or Ni-NTA His-Bind® Resin (Novagen) was added. Glutathione beads were washed three times with ice-cold PBS and resuspended in storage buffer (50 mM Hepes, pH 7.4, 150 mM NaCl, 5 mM DTT, 10% glycerol). Solid matrix bound MBD2b was kept at 4° C. for several weeks. Ni-NTA beads were washed and His-tagged MBD3L1 eluted according to the manufacturer's recommendations (Novagen). Eluted MBD3L1 was dialyzed against storage buffer (50 mM Hepes, pH 7.4, 150 mM NaCl, 5 mM DTT, 50% glycerol) and kept at −20° C. Purity and concentrations of the recombinant proteins were determined by SDS-PAGE and staining with Coomassie blue.

Cell Culture and DNA Purification

A549 cells were obtained from the American Type Culture Collection. The prostate epithelial cell lines 267B1 and Ki/HPV were obtained from Johng Rhim (Uniformed Services University of the Health Sciences, Bethesda, Md.). Mammalian cells were cultured in DMEM supplemented with 10% fetal bovine serum. Genomic DNA was purified from cells by a standard procedure using phenol chloroform extraction and ethanol precipitation. When the methylated-CpG island recovery assay (MIRA) procedure was started directly from cells, adherent cells were washed with cold PBS and scraped by using a rubber policeman. Scraped cells were centrifuged at 1000×g for 2 min at 4° C. and the cell pellet was resuspended in guanidinium hydrochloride containing binding buffer (Qiaquick PCR purification kit; Qiagen). Genomic DNA was sonicated in this solution to an average fragment length of 0.35 kb (corresponding to an average mass distribution of 0.7 kb on an ethidium-stained gel) and loaded onto the positively charged purification column (Qiaquick PCR purification kit; Qiagen). The bound fragment population was eluted according to the manufacturer's recommendations.

Methylated-CpG Island Recovery Assay (MIRA)

1 µg of GST or GST-tagged MBD2b protein bound to Glutathione Sepharose CL-4B matrix was incubated with sonicated and purified genomic DNA in the binding reaction mixture (10 mM Tris-HCl, pH 7.5, 50 mM NaCl, 1 mM EDTA, 1 mM DTT, 3 mM $MgCl_2$, 0.1% Triton-X100, 5% glycerol and 25 µg/ml BSA) for 20 min at 4° C. on a rocking platform. After washing the pelletted Sepharose beads three times with binding buffer containing 700 mM NaCl, the methylated DNA enriched genomic DNA fraction was eluted by addition of guanidinium hydrochloride containing buffer and purified using Qiaquick PCR purification kits (Qiagen). When His-tagged MBD3L1 was added to the binding reaction, a pre-incubation step (20 min at 4° C. on a rocking platform) was introduced before adding the sonicated genomic DNA. 1 µg of purified His-tagged MBD3L1 protein was added for the pre-incubation step.

PCR of CpG Islands

The RASSF1A promoter was amplified by using 20 pmoles of each primer: 5'-GCCAAGTGTGTTGCTTCAG-CAAACCG-3' (SEQ ID NO:2) and 5'-CCCGCAGCT-CAATGA GCTCAGGCT-3' (SEQ ID NO:3). For LINE-1 promoter detection the following primer pair was used: 5'-GCTCCGGTCTACAGCTCCCAGCGT-3' (SEQ ID NO:4) and 5'-AGCTGTGGTG GGCTCCACCCAGTT-3' (SEQ ID NO:5). The PCR reactions were performed according to the manufacturer's recommendations (Qiagen) using Q solution and 0.25 units of HotStart Taq enzyme per reaction. PCR cycling conditions were 92° C. for 20 sec, 60° C. for 30 sec and 72° C. for 30 sec. The optimal PCR cycle number was varied, but for starting the analysis an initial 28 cycles are suggested. The PCR products were separated by agarose gel electrophoresis. Using the MIRA approach, the result is an enrichment but not a complete purification of methylated-CpG islands that are bound by MBD2b. Therefore, the PCR reactions should be done in such a way that cycling is performed while the reaction is still in the linear stage of amplification.

Example 2

Methylated-CpG Island Recovery Assay (MIRA)

The methyl-CpG island recovery assay (MIRA) was developed as a GST pull-down method in which bacterially expressed and solid phase bound recombinant MBD2b protein is incubated with sonicated total genomic DNA. After washing of the beads with high salt buffer and elution of bound DNA, a gene-specific PCR reaction is performed on the isolated fragments to detect the recovered CpG islands (FIG. 1).

From recently published studies it is known that MBD2b possesses one of the highest affinities for methylated DNA among the MBD proteins (Fraga et al., 2003). MBD2b interacts with MBD3L1 and this interaction further strengthens MBD2b's binding affinity for methylated templates (Jiang et al., 2004). The MBD3L1 interaction domain was mapped to the C-terminal end of MBD2b, and therefore the full-length MBD2b protein and not just the MBD domain was used in the MIRA procedure. Methyl-CpG column chromatography has already proven that the MBD of MeCP2 immobilized to a solid matrix is suitable for selective retention of highly methylated CpG islands (Cross et al., 1994; Shiraishi et al., 1999). The tumor suppressor gene RASSF1A was cloned and characterized in our laboratory (Dammann et al., 2000) and it has been shown that its promoter is frequently methylated in many human cancer cell lines and primary tumors (Dammann et al., 2003a).

The recombinant proteins used in the subsequent experiments were first bacterially expressed and purified (FIG. 2A). Purified proteins were kept on the surface of Glutathione Sepharose beads at 4° C. until used. The sensitivity of MIRA for detection of the methylated RASSF1A promoter was next defined. From a previous study using bisulfite sequencing, it was known that the RASSF1A promoter is methylated in the A549 lung cancer cell line (Dammann et al., 2000). Sonicated DNA from the A549 cell line was mixed with solid matrix-bound GST-MBD2b and, as a negative control, with matrix-bound GST protein. Decreasing amounts of genomic DNA (1 µg, 0.5 µg, 0.25 µg, 0.125 µg, 0.062 µg, 0.031 µg, 0.025 µg, 0.01 µg and 0.001 µg) were added in the titration experiment. A positive signal for methylated DNA could be detected in the sample in which ~62 ng of DNA was added (FIG. 2B, lane 8). No signal was detected in samples containing only GST protein (FIG. 2B, lane 3) although the input DNA was the highest (1 µg).

MBD3L1 has significant homology to MBD2 and MBD3. Its MBD is missing and the protein can not bind to methylated DNA alone (Jiang et al., 2002). Recent in vitro binding experiments showed that MBD3L1 can interact with MBD2b and can enhance methylated-DNA-specific complex formation in a dose dependent manner (Jiang et al., 2004). To test whether the MBD3L1 protein's positive effect on MBD2b-methylated DNA complex formation can improve the sensitivity of the MIRA assay, matrix bound GST-MBD2b was preincubated with MBD3L1, and the detection efficiency was compared with that of reactions performed without MBD3L1 (FIG. 2C). It was found that MBD3L1 could increase the sensitivity of the assay and as low as 1 ng of input A549 DNA was sufficient to detect the methylated RASSF1A promoter (FIG. 2C, lane 12). The positive effect of MBD3L1 was not obvious at higher amounts of input DNA (FIG. 2C, lanes 5-8), but it was essential to detect the methylated-CpG island at lower amounts of input DNA (FIG. 2C, lanes 10 and 12). MBD3L1 protein could not provide methyl-CpG binding ability for GST protein in a control reaction (FIG. 2C, lane 4).

Figure 3:
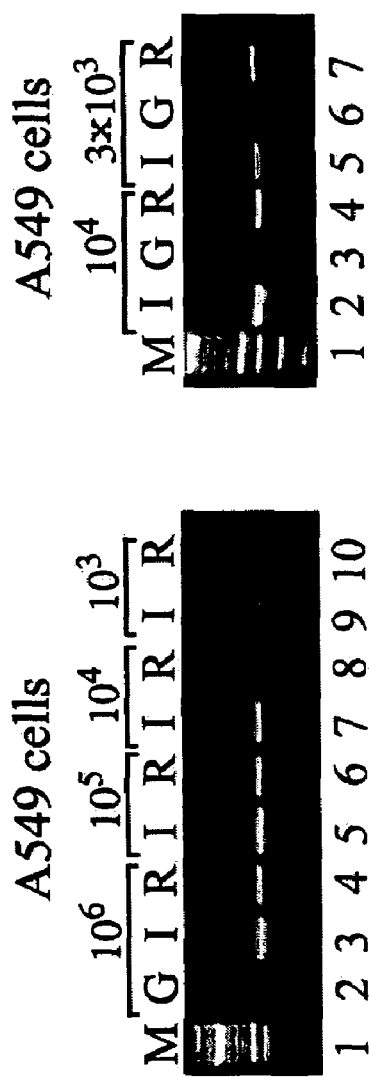
FIG. 3 shows MIRA of the RASSF1A promoter using small numbers of cells. Decreasing numbers of A549 cells were used in the assay. "G" and "R" refers to GST-only and GST-tagged MBD2b recovered samples. "I" stands for input DNA.

To further evaluate MIRA's sensitivity, the minimal cell number that is essential for detecting a hypermethylated RASSF1A promoter was determined (FIG. 3). A few thousand cells were sufficient to detect the methylated-CpG island of the RASSF1A promoter. $10^3$ cells were insufficient in this assay (FIG. 3A, lane 10) but $3 \times 10^3$ cells could provide a positive result (FIG. 3B, lane 7). In subsequent assays, $10^4$ cells per reaction were routinely used, and this number proved to be cell-type independent to provide sufficient amounts of input DNA (FIG. 4).

Figure 4:
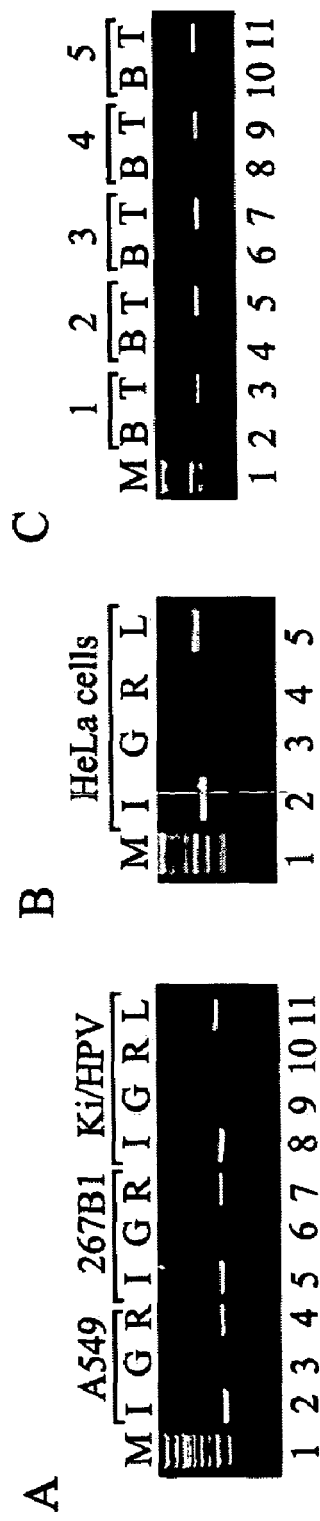
FIGS. 4A-4C show MIRA of the RASSF1A promoter using several cell lines and primary pancreatic cancer samples.

To appraise MIRA's usability in the diagnosis of cancer-specific DNA hypermethylation, the methylation status of the RASSF1A promoter in three additional cell lines was studied (FIG. 4). By analyzing different cell lines positive for RASSF1A promoter methylation (A549 and 267B1), results were obtained that exactly coincided with previous MSP analysis (Dammann et al., 2000; Liu et al., 2005). It was found that the RASSF1A promoter was unmethylated in the HPV transformed Ki/HPV prostate epithelial cell line and in HeLa cells (FIG. 4A, lane 10 and FIG. 4B, lane 4), as previously shown by bisulfite-based techniques Dammann et al., 2000; Liu et al., 2005). In the case of failed detection of a methylation-specific signal in a tested sample, it was necessary to exclude the possibility that this result was not because of loss of the input DNA during the procedure. Therefore PCR reactions using a LINE element specific primer pair were performed. LINE elements are retrotransposons inserted into the human genome in many copies (Kazazian and Goodier, 2002) and are normally heavily methylated (Hata and Sakaki, 1997; Yang et al., 2004). Using this control, the unmethylated status of a CpG island of interest can be verified (FIG. 4A, lane 11;

FIG. 4B, lane 5). These findings further confirm that the MIRA approach is suitable for monitoring the methylation status of specific regions of the genome. It is advisable to always include positive and negative controls (known unmethylated and methylated DNA samples) as well as a GST-only control.

To provide more data to strengthen the usability of MIRA, the methylation pattern of the RASSF1A promoter in primary human tumor samples was tested. In these experiments blood DNA served as a negative (unmethylated) control. It was found that the RASSF1A promoter was heavily methylated in pancreatic tumor samples but not in the corresponding blood samples (FIG. 4C). The same results for methylation of these samples were obtained previously by MSP (Dammann et al., 2003b). Primary tumor samples often are mixtures of normal and cancer cells, making the detection more difficult. However, similar to MSP, MIRA is a positive detection assay for methylated DNA, and thus has the ability to detect methylated DNA even when the tumor cell population is outnumbered by normal cells in the sample or tissue.

The density of methylation can also affect the binding affinity of MBD proteins (Fraga et al., 2003). These facts can account for different PCR cycle numbers that may need to be applied for detecting methylated alleles in primary tumor samples. However, most often, the methylation of CpG islands, when it occurs in tumors and is associated with gene silencing, affects a large proportion of all CpG dinucleotides in a given CpG island (Dammann et al., 2000).

The lowest detection limit of the methylation-specific PCR reaction is around 1 ng of input DNA (Herman et al., 1996). The MIRA approach can also reach this sensitivity by adding MBD3L1 protein to the binding reaction (FIG. 2C, lane 12). Bisulfite modification of DNA is a time consuming procedure and the whole MSP approach takes about two days. After having the purified recombinant proteins available, the MIRA approach provides data within about 3 hours (FIG. 1). The purified and immobilized GST-MBD2b protein can be stored in buffer at 4° C. for at least several weeks, while the His-tagged MBD3L1 protein can be kept in 50% glycerol containing buffer at −20° C. for several months without losing its activity. Taken together, the most time-consuming part of MIRA is the recombinant protein preparation, but after purifying reasonable amounts of the proteins the whole procedure is accomplished within only a few hours.

The sensitivity of MIRA is equivalent to MSP. It is a specific and sensitive but not laborious approach that can be clinically useful in detection and diagnosis of any DNA methylation related diseases including cancer.

Example 3

Testing of the Binding Capacity of the MIRA Matrix

Testing of the Binding Capacity of the MIRA Matrix

MIRA analysis was performed on 500 ng of input DNA after mixing 375, 250, 125 ng, and 0 ng of A549 DNA with 0 ng, 125, 250 and 375 ng of HeLa DNA, respectively. Supernatant fractions were concentrated using Qiaquick column (QIAGEN) according to the manufacturer's instructions. One µg of sonicated herring sperm DNA was added to the isolated DNA samples and these were treated with sodium bisulfite (Herman et al., 1996). The bisulfite-modified templates were monitored by methylation-specific PCR. For methylation-specific PCR analysis of the RASSF1A promoter the following primer pairs were used: METFor: 5'-GGGTTTTGC-GAGAGCGCG-3' (SEQ ID NO:6) and METRev: 5'-GCCCCAATACTAAATC ACGACG-3' (SEQ ID NO:7); UNMFor: 5'-GGGGTTTTGTGAGAGTGTGTTTAG-3' (SEQ ID NO:8) and UNMRev: 5'-TAAACACTAACAAA-CACAAACCAAAC-3' (SEQ ID NO:9).

Bisulfite Sequencing Analysis

MIRA was performed on pre-mixed 250 ng of A549 DNA (methylated RASSF1A promoter) and 250 ng of HeLa DNA (unmethylated RASSF1A promoter). DNA was purified from the supernatant and the pellet fraction. 1 µg of sonicated herring sperm DNA was added and sodium bisulfite treatment was performed on these samples. The RASSF1A promoter was amplified by semi-nested PCR. In the first PCR we used primer MU379 (5'-GTTTTGGTAGTT TAATGAGTTTAG-GTTTTTT-3'; SEQ ID NO:10) and primer ML370 (5'-AC-CCTCTTCCTCT AACACAATAAAACTAACC-3'; SEQ ID NO: 11). These primers amplify both unmethylated and methylated bisulfite-converted DNA templates. 1/50 volume of the first reaction was used as input in the second round of PCR. The internal primer MU561 (5'-CCCCACAATC-CCTAC ACCCAAAT-3'; SEQ ID NO:12) and the MU379 primers were used for amplification. The PCR products were cloned into the pDrive cloning vector (Qiagen) and 10 randomly selected recombinant clones were sequenced from the supernatant and pellet fraction, respectively.

Figure 5:
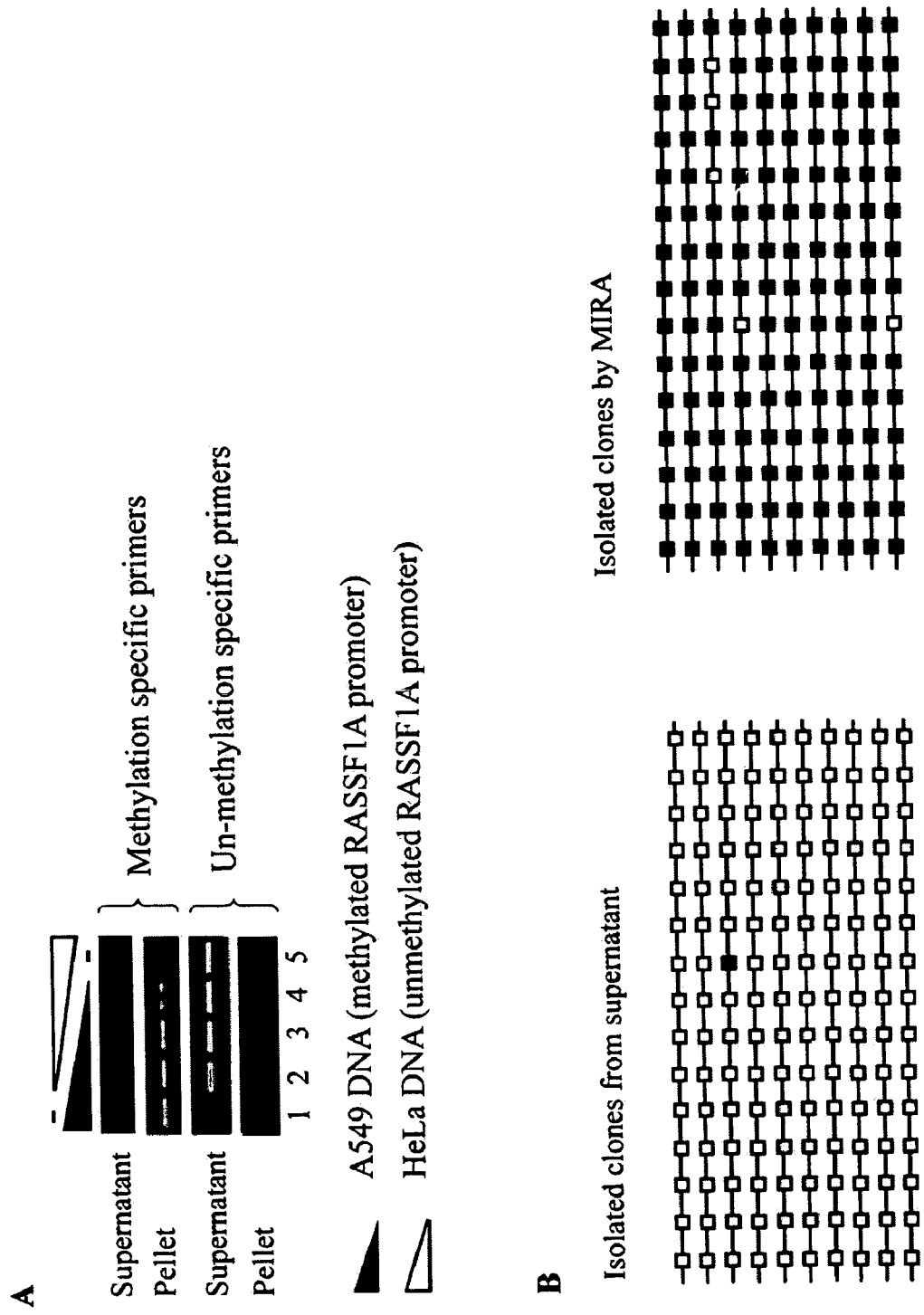
FIGS. 5A and 5B show the analysis of bisulfite-modified templates.

The binding capacity of the immobilized GST-MBD2b/MBD3L1 complex was tested in order to determine the lowest amount of input DNA where no methylated DNA is detectable in the supernatant after performing a MRA assay. First, different amounts of genomic DNA were mixed with a methylated RASSF1A promoter (from A549 cells) and unmethylated RASSF1A promoter (from HeLa cells), in such a way that the amount of input DNA was kept constant. Using the pre-mixed DNA the assay was performed, and the supernatant (unbound) and the pellet (bound) fractions were treated with sodium bisulfite. The bisulfite-modified templates were analyzed by methylation-specific PCR (MSP) (FIG. 5A). A methylated promoter signal in the supernatant fraction could not be detected even in the sample with the highest input of methylated DNA (500 ng), while the pellet (bound) fraction was positive even in the case of the lowest input sample (125 ng). The interpretation of this result is that the MBD2b/MBD3L1 complex has a very high binding capacity and can deplete the supernatant from methylated templates. The input amount of GST-MBD2b protein was about 1 µg, which is equivalent to about 15 pmoles of protein, while the amount of the input DNA is in the femtomolar range. The result was further verified by bisulfite sequencing analysis (FIG. 5B). The bisulfite-treated and PCR-amplified fragments from the supernatant and pellet fractions obtained from a mix of 50% unmethylated and 50% methylated DNA were cloned and sequenced. The amplified RASSF1A promoter fragment consists of 208 base pairs and contains fifteen potential CpG methylation sites. The vast majority of these sites were methylated in clones isolated from the pellet fraction, while none of them was appreciably methylated in the supernatant fraction (FIG. 5B). According to these data the input MBD2b/MBD3L1 complex has a high and specific capacity to bind methylated CpG containing sequences.

Example 4

Testing of the Effect of Methylation Density on MIRA

A PCR-amplified and purified RASSF1A promoter fragment was in vitro methylated with SssI or HpaII methyltransferase (New England Biolabs). One ng of the artificially methylated promoter and 100 ng of sonicated JM110 bacterial DNA were added to the binding reaction in the MIRA assay. Appearance of the methylation-specific signal in the bound fraction was analyzed after 20, 25, and 30 PCR cycles.

Although it has already been demonstrated that MBD2 can even recognize a single methylated CpG dinucleotide and the frequency of methyl-CpGs has an effect on binding (Fraga et al., 2003), how the density of methyl-CpGs influences the binding affinity of the MBD2b/MBD3L1 complex in MIRA was investigated. Promoter fragments artificially methylated with SssI or HpaII enzymes were used in the assay. There are 33 potential 5'CpG sites for SssI methylase and only 5 5'CCGG sites for HpaII methylase in the analyzed RASSF1A promoter fragment. The appearance of the specific signal at lower PCR cycle numbers was observed with the more densely methylated SssI template (FIG. 6). This result means that the density of the methyl-CpG dinucleotides may influence the assay's sensitivity, although low density methylation can be detected at higher PCR cycle numbers.

Example 5

Analysis of GSTP1 Promoter Methylation by MIRA

DNA samples were obtained from prostate cancer tissues and from normal blood samples as a control. For amplification of the GSTP1 promoter after enrichment of methylated DNA by MIRA, the following primers were used 5'-CCCGGGGTGCAGCGGCCGCC-3' (SEQ ID NO:13) and 5'-GCCCCAGTGCTGAGTCACGGCG-3' (SEQ ID NO: 14). PCR was carried out with 35 amplification cycles.

Figure 7:
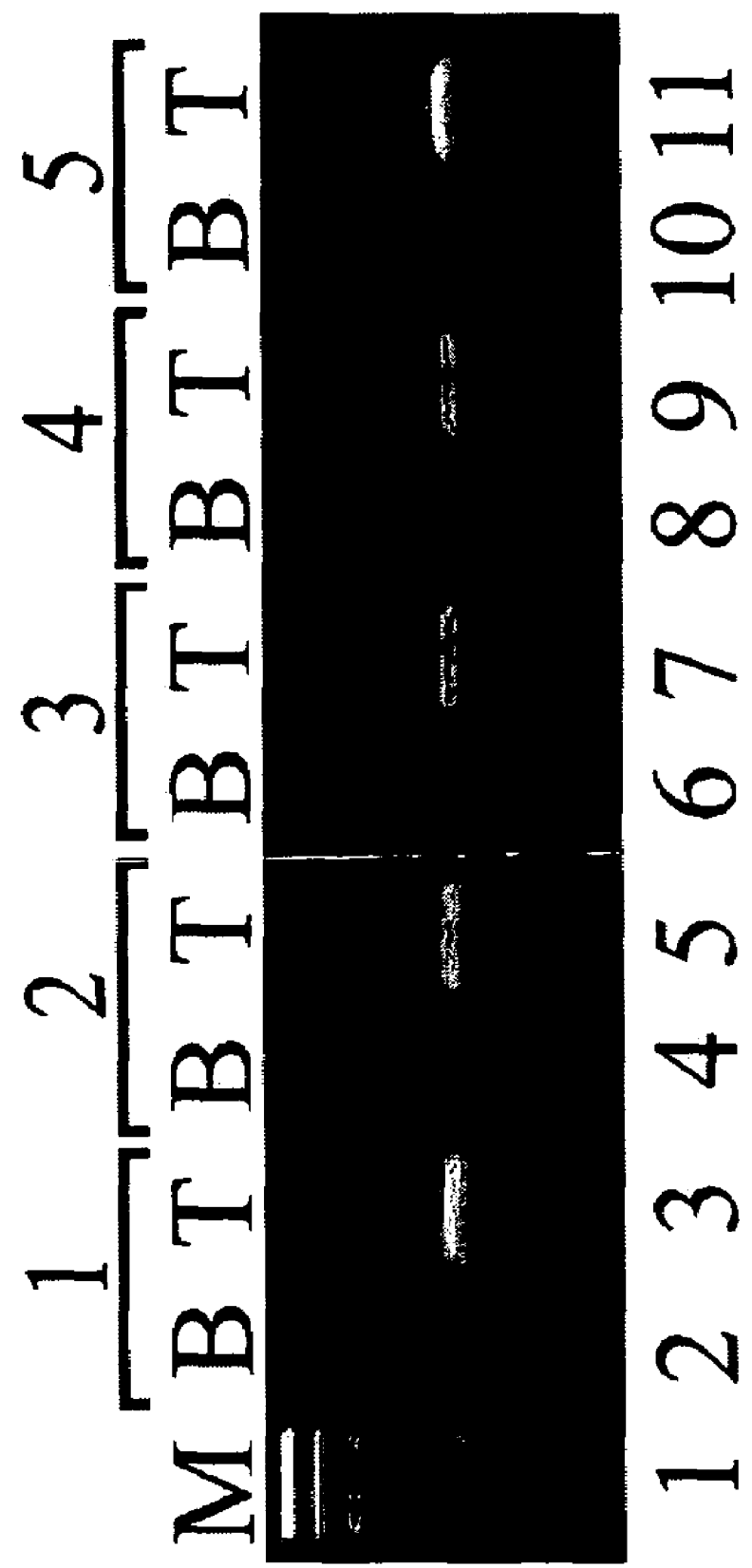
FIG. 7 shows the analysis of GSTP1 promoter methylation by MIRA. MIRA of the GSTP1 promoter was performed on 15 ng of sonicated blood (B) or prostate tumor (T) DNA samples.

The studies were extended to the GSTP1 promoter to further prove MIRA's usability (FIG. 7). Promoter methylation of the GSTP1 gene is a highly specific marker of prostate cancer (Yegnasubramanian et al., 2004). Genomic DNA was purified from prostate cancer samples and MIRA was performed on those templates and blood DNA served as a negative control. Consistent with previous studies (Yegnasubramanian et al., 2004) the data verifed that the GSTP1 promoter is frequently methylated in prostate cancer samples. According to the data obtained with the RASSF1A and GSTP1 promoters, MIRA can be used to analyze the methylation status of any CpG island.

Example 6

MIRA-Assisted Microarray Analysis

Experimental Procedures

DNA obtained from normal human bronchial epithelial (NHBE) cells and from the lung cancer cell line A549 was digested with MseI (5'-TTAA), which produces small (~200-300 bp) fragments and cuts outside of CpG islands. Linkers (upper strand sequence 5'-TAGAATTCAGATCTCCCG (SEQ ID NO:15); lower strand sequence 3'-CTTAAGTCTAGA-GGGCCCAGTGGCG (SEQ ID NO: 16)) were ligated to the MseI digested DNA and enrichment of the methylated fraction was done by MIRA as described above.

Briefly, 1 μg of purified GST-tagged MBD2b protein and 1 μg of purified His-tagged MBD3L1 protein were pre-incubated and bound to a Glutathione Sepharose CL-4B matrix. This matrix was incubated with MseI-cut and linker-ligated genomic DNA in a binding reaction mixture (10 mM Tris-HCl, pH 7.5, 50 mM NaCl, 1 mM EDTA, 1 mM DTT, 3 mM $MgCl_2$, 0.1% Triton-X100, 5% glycerol, 25 μg/ml BSA and 1.25 μg/ml sonicated JM110 DNA) for 240 min at 4° C. on a rocking platform. After washing the pelletted Sepharose beads three times with binding buffer containing 700 mM NaCl, the methylated DNA enriched genomic DNA fraction was eluted by addition of guanidinium hydrochloride containing buffer and purified using Qiaquick PCR purification kits (Qiagen).

The MIRA-captured DNA was then PCR-amplified using linker primers and was labeled with either Cy3-dCTP or Cy5-dCTP by random priming. In parallel, the MIRA-input DNA from normal and tumor DNA was labeled with either Cy3-dCTP or Cy5-dCTP by random priming (see scheme in FIG. 9B). Then the dye-labeled DNA samples were mixed and hybridized to the human CpG island microarrays using conditions specified by the manufacturer (UHN Microarray Centre, University of Toronto, Canada). The sequences present on this array are derived from a CpG island library in which 68% of the unique sequences map to the 5' end of known or putative genes (Cross et al., 1994; Heisler et al., 2005). 500+500 ng of MIRA enriched and input DNA labeled with either Cy5-dCTP or Cy3-dCTP, respectively, was mixed and hybridized to the CpG island arrays (see FIG. 12).

After washing, the slides were scanned using an Axon GenePix 4000b scanner and images were quantified by GenePix pro v.6 software. Preprocessing of raw data and statistical analysis were performed using Bioconductor packages in R programming environment. The spots marked as "bad" or "not found" by the GenePix software were excluded. Background correction was performed using the "normexp" method implemented in the Bioconductor LIMMA package to adjust the local median background estimates. The background-corrected intensity data were normalized using the Print-tip group Lowess method to remove the bias within each array. The dye bias was then further corrected by averaging the log2 ratios between the dye swap pairs. Based on our experience, the combined Lowess and dye swap normalization approach can best reduce variability. CpG island methylation profiles were determined by ratios between MIRA-enriched and un-enriched samples (enrichment factor) for both tumor and normal tissues. The ratios of the enrichment factors between cancer and normal DNA samples will measure the methylation difference between cancer and normal tissue.

To identify the CpG islands that are differentially methylated between normal and tumor cell DNA, methylation profiles were compared using statistical linear model in LIMMA. P values were not adjusted for multiple testing to control the false discovery rate. For target gene selection, un-adjusted P values were set at a level of 0.05, and the fold-change between cancer MIRA/Input vs. normal MIRA/Input (difference factor) was set at >2. Direct comparison of MIRA-enriched fractions from tumor and normal tissue DNA provided independent confirmation for the methylation differences observed, although differences in relative copy number of gene loci between the two genomes may affect the latter analysis.

Results

The MIRA-assisted microarray technique was applied to identify CpG islands methylated in the lung cancer cell line A549 relative to normal human bronchial epithelial (NHBE) cells (FIGS. 9C and 9D). Using the data obtained from such arrays, a list of genes was compiled that show hypermethylation in A549 cells relative to NHBE cells (Table 1). Most of the differentially methylated CpG islands mapped either close to the 5' ends of known or predicted genes or mapped to exons/introns and may represent regulatory elements. Interestingly, 8 of the top 46 hits, with a more than a 2-fold enrichment of the methylated fraction in A549 versus NHBE cell DNA, were mapped to homeobox genes (LHX2, LHX4, LBX1, PAX7, HOXB13, SIX2, HOXD3, and DLX1 (see Table 1). Individual homeobox genes have been reported to be methylated in tumors of various histological origins including lung cancer (Shiraishi et al., 2002b). The data indicate that simultaneous methylation of a series of homeobox genes on different chromosomes occurs in A549 lung cancer cells.

and Esophageal Cancers") and maps to chromosome 3p21.3, a common hotspot for loss of heterozygosity (LOH) and deletions in lung cancer and other solid tumors. DLEC1 encodes a protein of 1755 amino acids with unknown function (Daigo et al., 1999). To investigate if methylation of DLEC1 is present in human primary lung tumors, a series of

TABLE 1

Methylated Target Genes Identified by MIRA Microarray Analysis

| Target # | ID | FC Difference[a] | Genome Location | Distance[b] | Gene Symbol | Description |
|---|---|---|---|---|---|---|
| 1 | 1_A_12 | 4.72 | chr2: 175033605-175034788 | 0 | GRP155 | G protein-coupled receptor 155 |
| 2 | 18_E_17 | 4.34 | chr3: 38055590-38056657 | 0 | DLEC1 | Deleted in lung and esophageal cancer 1 |
| 3 | 1_B_19 | 3.69 | chr1: 176933895-176934835 | 0 | LHX4 | LIM homeobox 4 |
| 4 | 15_G_6 | 3.58 | chr1: 114111744-114111847 | 0 | PTPN22 | Protein tyrosine phosphatase |
| 5 | 8_E_7 | 3.54 | chr12: 14237814-14238207 | >30 kb | | |
| 6 | 25_H_18 | 3.53 | chr14: 23904920-23905609 | 1650 bp 5' | NFATC4 | Cytoplasmic nuclear factor of activated T-cells |
| 7 | 22_N_10 | 3.31 | chr6: 100542633-100542762 | 0 | GRP145 | G protein-coupled receptor 145 |
| 8 | 31_L_22 | 3.28 | chr6: 115099013-115099186 | >30 kb | | |
| 9 | 25_N_11 | 3.24 | chr10: 42569409-42570107 | 0 | hmm7851 | Hypothetical protein |
| 10 | 13_P_8 | 3.16 | chr6: 99402311-99402598 | 0 | hmm33765 | Hypothetical protein |
| 11 | 31_L_21 | 3.11 | chr6: 115099013-115099186 | >30 kb | | |
| 12 | 26_M_12 | 3.00 | chr13: 49163567-49163905 | 0 | EBPL | Emopamil binding related protein |
| 13 | 17J_9 | 2.92 | chr6: 45327693-45327793 | 0 | SUPT3H | SUPT3H protein |
| 14 | 25_0_20 | 2.78 | chrX: 48441921-48442544 | 2.5 kb 5' | ERAS | Small GTPase protein E-Ras |
| 15 | 17J_20 | 2.76 | chr9: 123856765-123857465 | 0 | LHX2 | LIM homeobox 2 |
| 16 | 7_L_22 | 2.65 | chr5: 72775997-72776155 | 3 kb 3' | FOXD1 | Forkhead transcription factor |
| 17 | 23_B_15 | 2.63 | chr8: 91679368-91679403 | >30 kb | | |
| 18 | 29_A_11 | 2.63 | chr1: 18716744-18718019 | 0 | PAX7 | Paired box gene 7 |
| 19 | 26_M_11 | 2.62 | chr12: 55167740-55168302 | 0 | GLS2 | Glutaminase 2 (liver, mitochondrial) |
| 20 | 7_K_7 | 2.58 | chr17: 44187113-44188088 | 26 kb 5' | HOXB13 | Homeobox gene |
| 21 | 29_A_6 | 2.58 | chr4: 136284675-136284784 | >30 kb | | |
| 22 | 2_B_9 | 2.54 | chr10: 102972869-102973961 | 2.5 kb 3' | LBX1 | Homeobox transcription factor |
| 23 | 21_0_20 | 2.45 | chr2: 45139996-45140793 | 3.6 kb 3' | SIX2 | Sine oculis homeobox homolog 2 |
| 24 | 21_E_12 | 2.45 | chr12: 48026625-48026800 | 0 | FLJ 13236 | Hypothetical protein FLJ 13236 |
| 25 | 2_A_10 | 2.40 | chr10: 102972869-102973961 | 0 | BRACE2016602 | Hypothetical protein |
| 26 | 14_J_18 | 2.38 | chr5: 83154024-83154192 | 0 | hmm32907 | Hypothetical protein |
| 27 | 12_B_24 | 2.35 | chr1: 16757837-16758127 | 0 | hmm16852 | Hypothetical protein |
| 28 | 22_L_21 | 2.34 | chr20: 28164999-28165149 | 0 | hmm117175 | Hypothetical protein |
| 29 | 7J_8 | 2.32 | chr6: 91594928-91595364 | >30 kb | | |
| 30 | 25_C_14 | 2.30 | chr4: 109450308-109450511 | 3.1 kb 5' | LEF1 | Lymphoid enhancer binding factor-1 |
| 31 | 25_'-22 | 2.28 | chr19: 4279686-4280325 | 0 | STAP2 | Signal-transducing adaptor protein 2 |
| 32 | 14_C_16 | 2.26 | chr6: 144647977-144648462 | 0 | hmm33914 | Hypothetical protein |
| 33 | 32_G_18 | 2.26 | chr5: 139908213-139908494 | 0 | EIF4EBP3 | Eukaryotic translation initiation factor 4E |
| 34 | 15_M_17 | 2.25 | chr22: 27793134-27793763 | 0 | KREMEN1 | KREMEN1 protein |
| 35 | 30_E_8 | 2.24 | chr5: 54551833-54552394 | 0 | CR626610 | Hypothetical protein |
| 36 | 14_N_16 | 2.21 | chr2: 176847561-176847721 | 6 kb 5' | HOXD3 | Homeobox gene HOXD3 |
| 37 | 18_E_9 | 2.19 | chr10: 102972869-102973961 | 2.5 kb 3' | LBX1 | Homeobox transcription factor |
| 38 | 20_0_10 | 2.16 | chr2: 172770466-172770678 | 4 kb 5'" | DLX1 | Homeobox protein DLX-1 |
| 39 | 15_J_24 | 2.15 | chr4: 88700602-88701596 | 0 | NUDT9 | Nucleoside diphosphate linked moiety X-type 9 |
| 40 | 14_L_15 | 2.13 | chr7: 154669328-154670208 | 0 | hmm78131 | Hypothetical protein |
| 41 | 20_L_5 | 2.07 | chr15: 39592659-39593447 | 0 | LTK | Leukocyte tyrosine kinase |
| 42 | 23_H_10 | 2.07 | chr8: 145671696-145672153 | 1.4 kb 5' | KIFC2 | Kinesin motor |
| 43 | 12_C_14 | 2.02 | chr11: 73167747-73168609 | 18 kb 5' | RAB6A | Small GTPase |
| 44 | 31_G_9 | 2.00 | chr17: 70443461-70443780 | 0 | OTOP3 | Otopetrin-3 |
| 45 | 1J_7 | 2.00 | chr9: 134057749-134059156 | 3 kb 3' | WDR5 | WD repeat domain 5 |
| 46 | 26_N_12 | 2.00 | chr1: 148695088-148695652 | 0 | THEM4 | Negative regulator of AKT |

[a]FC Difference is the ratio (fold-change) of MIRA-enriched over un-enriched (input) A549 DNA versus MIRA-enriched over un-enriched (input) NHBE DNA.
[b]A distance of "0" indicates that the taraet falls within a aene includina 500 bp upstream of its transcription start site.
Target information was verified using the UCSC Genome Browser and GenBank.

Figure 10:
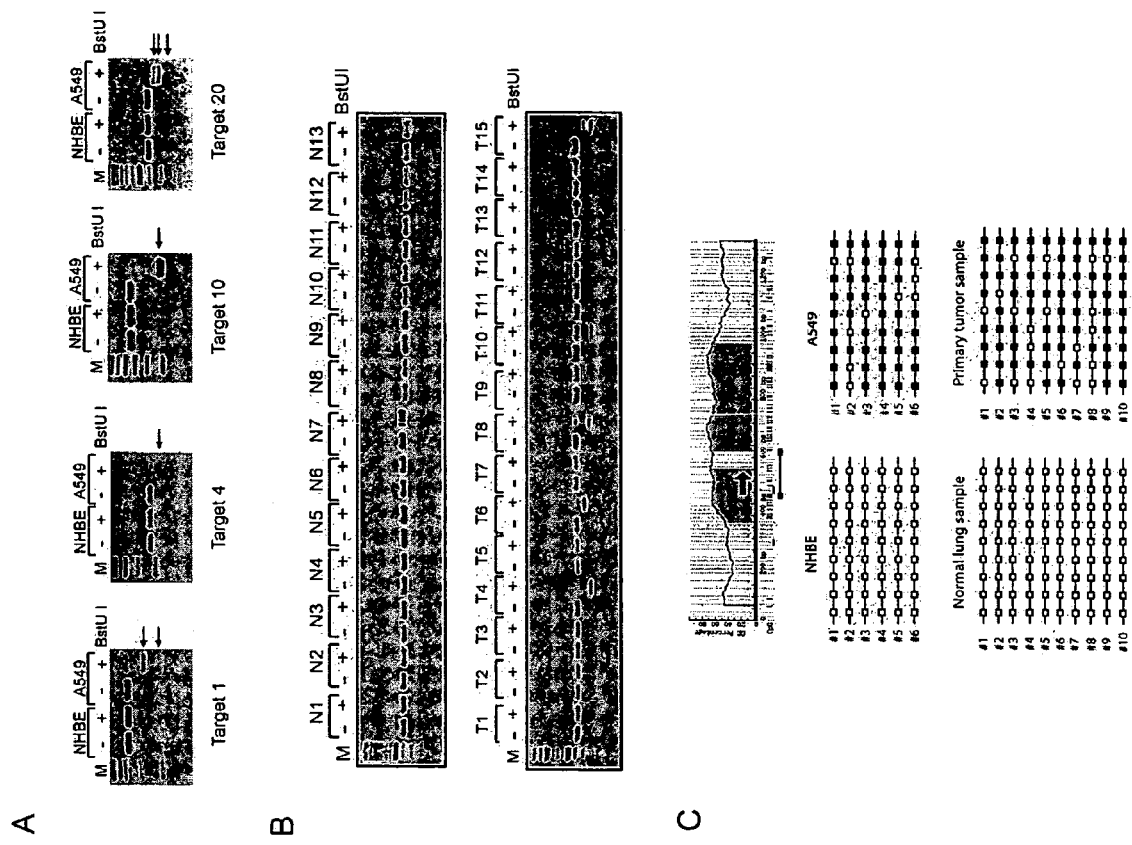
FIGS. 10A-10C show the confirmation of methylation differences and identification of DLEC1 as a target for tumor-specific methylation.

Cancer cell-specific methylation and lack of methylation in NHBE cells for several of the targets identified by the microarray analysis was confirmed using a BstUI COBRA assay (FIG. 10A). In this assay, a restriction endonuclease cleavage site is conserved after bisulfite treatment when the DNA is methylated (Xiong and Laird, 1997). COBRA assays confirmed the methylation of targets ranked number 1, 4, 10, and 20 on the list of differentially methylated genes confirming the robustness of the MIRA microarray approach. Several target genes were of particular interest. One methylated gene (Target 2 in Table 1) is designated as DLEC1 (Deleted in Lung 30 primary non-small cell lung cancers (NSCLCs) was analyzed by the COBRA assay (examples are shown in FIG. 10B) and by bisulfite sequencing (FIG. 10C). Eight of the 30 undissected tumor samples (=27%) tested (e.g., T4, T6, T8, T9, T10 and T15; FIG. 10B) showed clear evidence of methylation. None of the adjacent, tumor-matched, normal tissues had methylation of DLEC1 (FIGS. 10B and 10C). Using sodium bisulfite sequencing (Clark et al., 1994), we verified that the DLEC1-associated CpG island was highly methylated in A549 cells and in a primary lung tumor but was completely unmethylated in NHBE cells or normal lung tissue (FIG. 10C). Methylation encompassed the entire CpG island of DLEC1 (FIG. 10C and data not shown). In addition, the DLEC1 promoter was methylated in 3 out of 15 (=20%) primary esophageal cancers and in 3 of 10 (=30%) primary melanomas tested (FIGS. 11A and 11B).

In summary, the data shows that the MIRA-microarray approach has the ability to identify genes methylated in human tumors on a genome-wide basis. This technology is expected to be widely applicable for comprehensive analysis of DNA methylation patterns using available spotted microarrays and new generation genome-scanning arrays currently under development. Since this technique is straightforward and does not require complicated manipulations, it should easily be applicable in a clinical setting and should become useful as a diagnostic tool to classify tumors according to DNA methylation patterns on a genomic scale. In addition, this technology may aid in the identification of new candidate tumor suppressor genes and potential DNA methylation markers.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive. It will also be appreciated that in this specification and the appended claims, the singular forms of "a," "an" and "the" include plural reference unless the context clearly dictates otherwise. It will further be appreciated that in this specification and the appended claims, The term "comprising" or "comprises" is intended to be open-ended, including not only the cited elements or steps, but further encompassing any additional elements or steps.

BIBLIOGRAPHY

Barringer, K. J. et al. (1990). Blunt-end and single-strand ligations by Escherichia coli ligase: influence on an in vitro amplification scheme. *Gene,* 89, 117-122.

Baylin, S. B. et al. (1998). Alterations in DNA methylation: a fundamental aspect of neoplasia. *Adv Cancer Res,* 72, 141-196.

Bird, A. P. (1986). CpG-rich islands and the function of DNA methylation. *Nature,* 321, 209-213.

Chen, W. Y. et al. (2003). Heterozygous disruption of Hic1 predisposes mice to a gender-dependent spectrum of malignant tumors. *Nat Genet* 33, 197-202.

Ching, T. T. et al. (2005). Epigenome analyses using BAC microarrays identify evolutionary conservation of tissue-specific methylation of SHANK3. *Nat Genet* 37, 645-651.

Clark, S. J. et al. (1994). High sensitivity mapping of methylated cytosines. *Nucleic Acids Res,* 22, 2990-2997.

Costello, J. F. et al. (2000). Aberrant CpG-island methylation has non-random and tumour-type-specific patterns. *Nat Genet,* 24, 132-138.

Cross, S. H. et al. (1994). Purification of CpG islands using a methylated DNA binding column. *Nat Genet,* 6, 236-244.

Cui, H. et al. (2003). Loss of IGF2 imprinting: a potential marker of colorectal cancer risk. *Science* 299, 1753-1755.

Daigo, Y. et al. (1999). Molecular cloning of a candidate tumor suppressor gene, DLC1, from chromosome 3p21.3. *Cancer Res* 59, 1966-1972.

Dammann, R. et al. (2000). Epigenetic inactivation of a RAS association domain family protein from the lung tumour suppressor locus 3p21.3. *Nature Genet,* 25, 315-319.

Dammann, R. et al. (2003a). Epigenetic inactivation of the Ras-association domain family 1 (RASSF1A) gene and its function in human carcinogenesis. *Histol Histopathol,* 18, 665-677.

Dammann, R. et al. (2003b). Frequent RASSF1A promoter hypermethylation and K-ras mutations in pancreatic carcinoma. *Oncogene,* 22, 3806-3812.

Dammann, R. et al. (2005). The tumor suppressor RASSF1A in human carcinogenesis: an update. *Histol Histopathol,* 20, 645-663.

Eckert, K. A. and T. A. Kunkel (1991). DNA polymerase fidelity and the polymerase chain reaction. *PCR Methods and Applications,* 1, 17-24.

Esteller, M. et al (2001). A gene hypermethylation profile of human cancer. *Cancer Res,* 61, 3225-3229.

Esteller, M. (2002). CpG island hypermethylation and tumor suppressor genes: a booming present, a brighter future. *Oncogene,* 21, 5427-5440.

Feinberg, A. P. and B. Vogelstein, (1983). Hypomethylation distinguishes genes of some human cancers from their normal counterparts. *Nature,* 301, 89-92.

Fraga, M. F. and Esteller, M. (2002). DNA methylation: a profile of methods and applications. *Biotechniques,* 33, 632, 634, 636-649.

Fraga, M. F. et al. (2003). The affinity of different MBD proteins for a specific methylated locus depends on their intrinsic binding properties. *Nucleic Acids Res,* 31, 1765-1774.

Frommer, M. et al. (1992). A genomic sequencing protocol that yields a positive display of 5-methylcytosine residues in individual DNA strands. *Proc Natl Acad Sci USA,* 89, 1827-1831.

Fujii, H. et al. (1998). Methylation of the HIC-1 candidate tumor suppressor gene in human breast cancer. *Oncogene* 16, 2159-2164.

Guatelli, J. C. et al. (1990). Isothermal, in vilro amplification of nucleic acids by a multienzyme reaction modeled after retroviral replication. *Proc Natl Acad Sci USA,* 87, 1874-1878. Erratum in: *Proc Natl Acad Sci USA,* 87, 7797 (1990).

Hanada, M. et al. (1993). bcl-2 gene hypomethylation and high-level expression in B-cell chronic lymphocytic leukemia. *Blood,* 82, 1820-1828.

Hata, K. and Sakaki, Y. (1997). Identification of critical CpG sites for repression of L1 transcription by DNA methylation. *Gene,* 189, 227-234.

Heisler, L. E. et al. (2005). CpG Island microarray probe sequences derived from a physical library are representative of CpG Islands annotated on the human genome. *Nucleic Acids Res* 33, 2952-2961.

Hendrich, B. and Bird, A. (1998). Identification and characterization of a family of mammalian methyl-CpG binding proteins. *Mol Cell Biol,* 18, 6538-6547.

Hendrich, B. and Bird, A. (2000). Mammalian methyltransferases and methyl-CpG-binding domains: proteins involved in DNA methylation. *Curr Top Microbiol Immunol,* 249, 55-74.

Herman, J. G. et al. (1995). Inactivation of the CDKN2/p16/MTS1 gene is frequently associated with aberrant DNA methylation in all common human cancers. *Cancer Res* 55, 4525-4530.

Herman, J. G. et al. (1996). Methylation-specific PCR: a novel PCR assay for methylation status of CpG islands. *Proc Natl Acad Sci USA,* 93, 9821-9826.

Huang, et al. (1999). Methylation profiling of CpG islands in human breast cancer cells. *Hum Mol Genet,* 8, 459-470.

Jiang, C. L. et al. (2002). MBD3L1 and MBD3L2, two new proteins homologous to the methyl-CpG-binding proteins MBD2 and MBD3: characterization of MBD3L1 as a testis-specific transcriptional repressor. *Genomics*, 80, 621-629.

Jiang, C. L. et al. (2004). MBD3L1 is a transcriptional repressor that interacts with methyl-CpG-binding protein 2 (MBD2) and components of the NuRD complex. *J Biol Chem*, 279, 52456-52464.

Jones, P. A. and Baylin, S. B. (2002). The fundamental role of epigenetic events in cancer. *Nat Rev Genet*, 3, 415-428.

Kanai, Y. et al. (1999). DNA hypermethylation at the D17S5 locus and reduced HIC-1 mRNA expression are associated with hepatocarcinogenesis. *Hepatology* 29, 703-709.

Kazazian, H. H., Jr. and Goodier, J. L. (2002). LINE drive: retrotransposition and genome instability. *Cell*, 110, 277-280.

Keshet, I. et al. (2006). Evidence for an instructive mechanism of de novo methylation in cancer cells. *Nat Genet* 38, 149-153.

Klose, R. J. et al. (2005). DNA binding selectivity of MeCP2 due to a requirement for A/T sequences adjacent to methyl-CpG. *Mol Cell* 19, 667-678.

Kopp, M. U. et al. (1998). Chemical Amplification: Continuous Flow PCR on a Chip. *Science*, 280, 1046-1048.

Kwoh, D. Y. et al. (1989). Transcription-based amplification system and detection of amplified human immunodeficiency virus type 1 with a bead-based sandwich hybridization format. *Proc Natl Acad Sci USA*, 86, 1173-1177.

Landegren, U. et al. (1988). A ligase-mediated gene detection technique. *Science*, 241, 1077-1080.

Li, Q. L. et al. (2002). Causal relationship between the loss of RUNX3 expression and gastric cancer. *Cell* 109, 113-124.

Liu, L. et al. (2005). A methylation profile of in vitro immortalized human cell lines. *Int J Oncol*, 26, 275-285.

Mattila, P. et al. (1991). Fidelity of DNA synthesis by the Thermococcus litoralis DNA polymerase—an extremely heat stable enzyme with proofreading activity. *Nucleic Acids Res*, 19, 4967-4973.

Maxam, A. M. and Gilbert, W. (1980). Sequencing end-labeled DNA with base-specific chemical cleavages. *Methods Enzymol*, 65, 499-560.

Otterson, G. A. et al. (1995). CDKN2 gene silencing in lung cancer by DNA hypermethylation and kinetics of p16INK4 protein induction by 5-aza 2'deoxycytidine. *Oncogene*, 11, 1211-1216.

Pfeifer, G. P. et al. (1989). Genomic sequencing and methylation analysis by ligation mediated PCR. *Science*, 246, 810-813.

Rauch, T. and Pfeifer, G. P. (2005). Methylated-CpG island recovery assay: a new technique for the rapid detection of methylated-CpG islands in cancer. *Lab Invest* 85, 1172-1180.

Schmutte, C. and P. A. Jones (1998). Involvement of DNA methylation in human carcinogenesis. *Biol Chem*, 379, 377-388.

Shi, H. et al. (2003). Triple analysis of the cancer epigenome: an integrated microarray system for assessing gene expression, DNA methylation, and histone acetylation. *Cancer Res* 63, 2164-71.

Shiraishi, M. et al. (1999). Isolation of DNA fragments associated with methylated CpG islands in human adenocarcinomas of the lung using a methylated DNA binding column and denaturing gradient gel electrophoresis. *Proc Natl Acad Sci USA*, 96, 2913-2918.

Shiraishi, M. et al. (2002a). An overview of the analysis of DNA methylation in mammalian genomes. *Biol Chem*, 383, 893-906.

Shiraishi, M. et al. (2002b). HOX gene clusters are hotspots of de novo methylation in CpG islands of human lung adenocarcinomas. *Oncogene* 21, 3659-3662.

Singer, J. et al. (1979). Methylation of mouse liver DNA studied by means of the restriction enzymes msp I and hpa II. *Science*, 203, 1019-1021.

Suzuki, H. et al. (2002). A genomic screen for genes upregulated by demethylation and histone deacetylase inhibition in human colorectal cancer. *Nat Genet* 31, 141-149.

Wade, P. A. (2001). Methyl CpG binding proteins: coupling chromatin architecture to gene regulation. *Oncogene*, 20, 3166-3173.

Weber, M. et al. (2005). Chromosome-wide and promoter-specific analyses identify sites of differential DNA methylation in normal and transformed human cells. *Nat Genet* 37, 853-862.

Wu, D. Y and R. B. Wallace (1989). The ligation amplification reaction (LAR)—amplification of specific DNA sequences using sequential rounds of template-dependent ligation. *Genomics*, 4, 560-569.

Xiong, Z. and Laird, P. W. (1997). COBRA: a sensitive and quantitative DNA methylation assay. *Nucleic Acids Res*, 25, 2532-2534.

Yamashita, K. et al. (2002). Pharmacologic unmasking of epigenetically silenced tumor suppressor genes in esophageal squamous cell carcinoma. *Cancer Cell* 2, 485-495.

Yang, A. S. et al. (2004). A simple method for estimating global DNA methylation using bisulfite PCR of repetitive DNA elements. *Nucleic Acids Res*, 32, e38.

Yegnasubramanian, S. et al. (2004). Hypermethylation of CpG islands in primary and metastatic human prostate cancer. *Cancer Res* 64, 1975-1986.

What is claimed is:

1. A method of detecting methylated CpG islands which comprises:
   (a) purifying genomic DNA from a sample;
   (b) incubating a methylated CpG island binding protein, a binding partner for the binding protein, and the purified genomic DNA to produce bound DNA, wherein the bound DNA comprises genomic DNA having methylated CpG islands bound to the said binding protein, having bound the binding partner;
   (c) isolating the bound DNA; and
   (d) amplifying the bound DNA to detect methylated CpG islands.

2. The method of claim 1, wherein the genomic DNA has been fragmented prior to incubation.

3. The method of claim 2, wherein the genomic DNA is fragmented by sonication.

4. The method of claim 1, wherein the binding protein is bound to a solid phase.

5. The method of claim 1, wherein the binding protein is MBD2b or fission protein comprising MBD2b.

6. The method of claim 4, wherein the binding protein is MBD2b or fusion protein comprising MBD2b.

7. The method of claim 5, wherein the binding partner is MBD3L1.

8. The method of claim 6, wherein the binding partner is MBD3L1.

9. The method of claim 5, wherein the fusion protein is a fusion protein of GST and MBD2b.

10. The method of claim 9, wherein the binding partner is MBD3L1.

11. The method of claim 6, wherein the fusion protein is a fusion protein of GST and MBD2b.

12. The method of claim 11, wherein the binding partner is MBD3L1.

13. The method of claim 1 which further comprises the step of treating the bound DNA prior to amplification with an agent that modifies unmethylated cytosines.

14. The method of claim 1, wherein the genomic DNA is digested with a restriction endonuclease that cuts outside of CpG islands prior to step (b).

15. The method of claim 1, wherein the amplification is performed using labeled deoxynucleotides to produce a labeled amplification product.

16. The method of claim 15, which further comprises hybridizing the labeled amplification product to a CpG island-containing microarray to detect the methylated CpG islands.

17. A method of detecting methylated CpG islands which comprises:
   (a) isolating genomic DNA from a sample;
   (b) incubating MBD2b or a fusion protein comprising MBD2b, MBD3L1 and genomic DNA to produce bound DNA, wherein the bound DNA comprises genomic DNA containing methylated CpG islands bound to the MBD2b or the fusion protein comprising MBD2b and wherein the MBD2b or the fusion protein comprising MBD2b is bound to a solid phase;
   (c) eluting the bound DNA from the solid phase; and
   (d) amplifying the bound DNA to detect methylated CpG islands.

18. The method of claim 17, wherein the genomic DNA is fragmented by sonication prior to incubation.

19. The method of claim 17, wherein the MBD3L1 is pre-incubated with MBD2b or the fusion protein comprising MBD2b bound to the solid phase prior to the incubation with the genomic DNA.

20. The method of claim 17, wherein the fusion protein is a fusion protein of GST and MBD2b.

21. The method of claim 19, wherein the fusion protein is a fusion protein of GST and MBD2b.

22. The method of claim 17 which further comprises the step of treating the bound DNA prior to amplification with an agent that modifies unmethylated cytosines.

23. The method of claim 22, wherein the agent is bisulfite.

24. The method of claim 17, wherein the genomic DNA is digested with a restriction endonuclease that cuts outside of CpG islands prior to step (b).

25. The method of claim 17, wherein the amplification is performed using labeled deoxynucleotides to produce a labeled amplification product.

26. The method of claim 25 which further comprises hybridizing the labeled amplification product to a CpG island-containing microarray to detect the methylated CpG islands.

27. A method of detecting methylated CpG islands which comprises:
(a) isolating genomic DNA from a sample;
(b) fragmenting the genomic DNA by sonication or restriction endonuclease;
(c) incubating a solid phase containing MBD2b or a fusion protein comprising MBD2b with MBD3L1 such that MBD3L1 binds to the MBD2b or the fusion protein;
(d) incubating the fragmented genomic DNA and the MBD2b having bound MBD3L1 or the fusion protein comprising MBD2b having bound MBD3L1 to produce bound DNA, wherein the bound DNA comprises the fragmented genomic DNA containing methylated CpG islands bound to the MBD2b having bound MBD3L1 or the fusion protein comprising MBD2b having bound MBD3L1;
(e) eluting the bound DNA from the solid phase; and
(f) gene-specific amplifying the bound DNA to detect methylated CpG islands.

28. The method of claim 27, wherein the fusion protein is a fusion protein of GST and MBD2b.

29. The method of claim 27 which further comprises the step of treating the bound DNA prior to amplification with an agent that modifies unmethylated cytosines.

30. The method of claim 27, wherein the amplification is performed using labeled deoxynucleotides to produce a labeled amplification product.

31. The method of claim 30 which further comprises hybridizing the labeled amplification product to a CpG island-containing microarray to detect the methylated CpG islands.

32. A method of determining genome-wide methylation patterns which comprises:
(a) isolating genomic DNA from a sample;
(b) incubating a solid phase containing MBD2b or a fusion protein comprising MBD2b with MBD3L1 such that MBD3L1 binds to the MBD2b or the fusion protein comprising MBD2b;
(c) incubating the isolated genomic DNA and the MBD2b having bound MBD3L1 or the fusion protein comprising MBD2b having bound MBD3L1 to produce bound DNA, wherein the bound DNA comprises the genomic DNA containing methylated CpG islands bound to the MBD2b having bound MBD3L1 or the fusion protein comprising MBD2b having bound MBD3L1;
(d) eluting the bound DNA from the solid phase;
(e) amplifying the bound DNA;
(f) labeling the amplified bound DNA and input DNA;
(g) hybridizing the labeled amplified bound DNA and labeled input DNA to a CpG island-containing microarray; and
(h) analyzing the microarray to determine DNA methylation pattern.

33. The method of claim 32, wherein the genomic DNA is digested with a restriction endonuclease that cuts outside of CpG islands prior in step (c).

34. The method of claim 32, wherein the fusion protein is a fusion protein of GST and MBD2b.

35. The method of claim 32 which further comprises the step of treating the bound DNA prior to amplification with an agent that modifies unmethylated cytosines.

36. The method of claim 32, wherein the amplified bound DNA is labeled during amplification using labeled deoxynucleotides.

37. The method of claim 32, wherein the input DNA is DNA isolated from normal tissue, disease tissue or both.

38. The method of claim 32, wherein linkers are ligated to the genomic DNA prior to (e).

* * * * *

UNITED STATES PATENT AND TRADEMARK OFFICE
CERTIFICATE OF CORRECTION

PATENT NO. : 7,425,415 B2
APPLICATION NO. : 11/398765
DATED : September 16, 2008
INVENTOR(S) : Gerd P. Pfeifer et al.

It is certified that error appears in the above-identified patent and that said Letters Patent is hereby corrected as shown below:

On the Title Page item 56

Under OTHER PUBLICATIONS section, the Hendrich B. et al. reference (first occurrence) should be replaced with – Hendrich B. et al., "Mammalian Methyltranferases and Methyl-CpG-Binding Domains: Proteins Involved in DNA Methylation," pp. 55-74; Institute of Cell and Molecular Biology, University of Edinburgh, Darwin Building, King's Buildings, Edinburgh, Scotland, UK

In the Specification

Col. 1, line 12, "Grant Nos. CA88873 and CA104967" should read "Grant No. CA104967"

In the Claims

Col. 33, line 52, "fission" should read "fusion"

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 16

<210> SEQ ID NO 1
<211> LENGTH: 434
<212> TYPE: DNA
<213> ORGANISM: Homo sapiens

<400> SEQUENCE: 1
gccaagtgtg ttgcttcagc aaaccggacc aggagggcca gggccggatg tggggaccct      60
cttcctctag cacagtaaag ctggcctcca gaaacacggg tatctccgcg tggtgctttg     120
cggtcgccgt cgttgtggcc gtccggggtg gggtgtgagg aggggacgaa ggagggaagg     180
```

-continued

```
aagggcaagg cggggggggc tctgcgagag cgcgcccagc cccgccttcg ggccccacag    240
tccctgcacc caggtttcca ttgcgcggct ctcctcagct ccttcccgcc gcccagtctg    300
gatcctgggg gaggcgctga agtcgggggcc cgccctgtgg cccgcccgg ccgcgcttg     360 ctagcgccca aagccagcga agcacgggcc caaccgggcc atgtcggggg agcctgagct    420
cattgagctg cggg                                                     434
```

<210> SEQ ID NO 2
<211> LENGTH: 26
<212> TYPE: DNA
<213> ORGANISM: Artificial
<220> FEATURE:
<223> OTHER INFORMATION: Oligonucleotide primer

<400> SEQUENCE: 2

```
gccaagtgtg ttgcttcagc aaaccg                                         26
```

<210> SEQ ID NO 3
<211> LENGTH: 24
<212> TYPE: DNA
<213> ORGANISM: Artificial
<220> FEATURE:
<223> OTHER INFORMATION: Oligonucleotide primer

<400> SEQUENCE: 3

```
cccgcagctc aatgagctca ggct                                           24
```

<210> SEQ ID NO 4
<211> LENGTH: 24
<212> TYPE: DNA
<213> ORGANISM: Artificial
<220> FEATURE:
<223> OTHER INFORMATION: Oligonucleotide primer

<400> SEQUENCE: 4

```
gctccggtct acagctccca gcgt                                           24
```

<210> SEQ ID NO 5
<211> LENGTH: 24
<212> TYPE: DNA
<213> ORGANISM: Artificial
<220> FEATURE:
<223> OTHER INFORMATION: Oligonucleotide primer

<400> SEQUENCE: 5

```
agctgtggtg ggctccaccc agtt                                           24
```

<210> SEQ ID NO 6
<211> LENGTH: 18
<212> TYPE: DNA
<213> ORGANISM: Artificial
<220> FEATURE:
<223> OTHER INFORMATION: Oligonucleotide primer

<400> SEQUENCE: 6

```
gggttttgcg agagcgcg                                                  18
```

<210> SEQ ID NO 7
<211> LENGTH: 22
<212> TYPE: DNA
<213> ORGANISM: Artificial
<220> FEATURE:
<223> OTHER INFORMATION: Oligonucleotide primer

<400> SEQUENCE: 7
gccccaatac taaatcacga cg                                              22

<210> SEQ ID NO 8
<211> LENGTH: 24
<212> TYPE: DNA
<213> ORGANISM: Artificial
<220> FEATURE:
<223> OTHER INFORMATION: Oligonucleotide primer

<400> SEQUENCE: 8
ggggttttgt gagagtgtgt ttag                                            24

<210> SEQ ID NO 9
<211> LENGTH: 26
<212> TYPE: DNA
<213> ORGANISM: Artificial
<220> FEATURE:
<223> OTHER INFORMATION: Oligonucleotide primer

<400> SEQUENCE: 9
taaacactaa caaacacaaa ccaaac                                          26

<210> SEQ ID NO 10
<211> LENGTH: 31
<212> TYPE: DNA
<213> ORGANISM: Artificial
<220> FEATURE:
<223> OTHER INFORMATION: Oligonucleotide primer

<400> SEQUENCE: 10
gttttggtag tttaatgagt ttaggttttt t                                    31

<210> SEQ ID NO 11
<211> LENGTH: 31
<212> TYPE: DNA
<213> ORGANISM: Artificial
<220> FEATURE:
<223> OTHER INFORMATION: Oligonucleotide primer

<400> SEQUENCE: 11
accctcttcc tctaacacaa taaaactaac c                                    31

<210> SEQ ID NO 12
<211> LENGTH: 23
<212> TYPE: DNA
<213> ORGANISM: Artificial
<220> FEATURE:
<223> OTHER INFORMATION: Oligonucleotide primer

<400> SEQUENCE: 12
ccccacaatc cctacaccca aat                                             23

<210> SEQ ID NO 13
<211> LENGTH: 20
<212> TYPE: DNA
<213> ORGANISM: Artificial
<220> FEATURE:
<223> OTHER INFORMATION: Oligonucleotide primer

<400> SEQUENCE: 13
cccggggtgc agcggccgcc                                                 20

<210> SEQ ID NO 14
<211> LENGTH: 22
<212> TYPE: DNA

```
<213> ORGANISM: Artificial
<220> FEATURE:
<223> OTHER INFORMATION: Oligonucleotide primer

<400> SEQUENCE: 14
gccccagtgc tgagtcacgg cg                                              22

<210> SEQ ID NO 15
<211> LENGTH: 18
<212> TYPE: DNA
<213> ORGANISM: Artificial
<220> FEATURE:
<223> OTHER INFORMATION: Oligonucleotide linker

<400> SEQUENCE: 15
tagaattcag atctcccg                                                   18

<210> SEQ ID NO 16
<211> LENGTH: 25
<212> TYPE: DNA
<213> ORGANISM: Artificial
<220> FEATURE:
<223> OTHER INFORMATION: Oligonucleotide linker

<400> SEQUENCE: 16
cttaagtcta gagggcccag tggcg                                           25
```